United States Patent
Tsuruta et al.

(10) Patent No.: US 6,646,093 B2
(45) Date of Patent: Nov. 11, 2003

(54) WATER-SOLUBLE POLYURETHANE HAVING COMB-SHAPED HYDROPHOBIC GROUP AND APPLICATION THEREOF

(75) Inventors: Manabu Tsuruta, Sodegaura (JP); Masahiko Mitsuzuka, Sodegaura (JP); Yunzhi Wu, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 234 days.

(21) Appl. No.: 09/733,970

(22) Filed: Dec. 12, 2000

(65) Prior Publication Data

US 2002/0045724 A1 Apr. 18, 2002

(30) Foreign Application Priority Data

Apr. 7, 2000 (JP) ........................ 2000-105865

(51) Int. Cl.[7] ................ C08G 18/32; C08G 18/50; C08L 75/04; C08L 75/12; A61K 7/06

(52) U.S. Cl. .................. 528/78; 424/70.11; 524/2; 524/3; 524/4; 524/7; 524/442; 524/444; 524/591; 524/839; 524/840; 528/70; 528/85; 528/76; 528/77

(58) Field of Search .............. 424/70.11; 524/442, 524/444, 591, 839, 2, 3, 4, 7, 840; 528/70, 78, 85, 76, 77

(56) References Cited

U.S. PATENT DOCUMENTS

| | | | | |
|---|---|---|---|---|
| 3,926,867 A | * | 12/1975 | Quock et al. | 521/164 |
| 4,275,236 A | * | 6/1981 | Earl et al. | 564/298 |
| 4,426,485 A | | 1/1984 | Hoy et al. | 524/591 |
| 5,041,467 A | * | 8/1991 | Kataoka et al. | 521/99 |
| 6,515,050 B1 | * | 2/2003 | Mitsuzuka et al. | 568/704 |

FOREIGN PATENT DOCUMENTS

| | | |
|---|---|---|
| JP | B437134 | 9/1960 |
| JP | A57123850 | 8/1982 |
| JP | A5978226 | 5/1984 |
| JP | A10298261 | 11/1998 |

\* cited by examiner

*Primary Examiner*—Rabon Sergent
(74) *Attorney, Agent, or Firm*—Birch, Stewart, Kolasch & Birch, LLP

(57) ABSTRACT

Water-soluble polyurethane according to the present invention is obtained from polyalkylene glycols, diisocyanates, and comb-shaped hydrophobic diols represented by the following general formula (3):

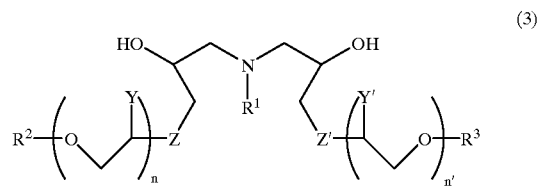

wherein each of $R^1$, $R^2$ and $R^3$ is a hydrocarbon group; each of Y and Y' is hydrogen, a methyl group or a $CH_2Cl$ group; each of Z and Z' is oxygen, sulfur or a $CH_2$ group; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group. The water-soluble polyurethane is used as, for example, an extruding auxiliary for cement materials, a mortar thickening agent, an underwater concrete thickening agent, a ceramics forming binder and a moisturizer for hair cosmetics, all of which are characterized by excellent water retention and high shape retention.

28 Claims, 4 Drawing Sheets

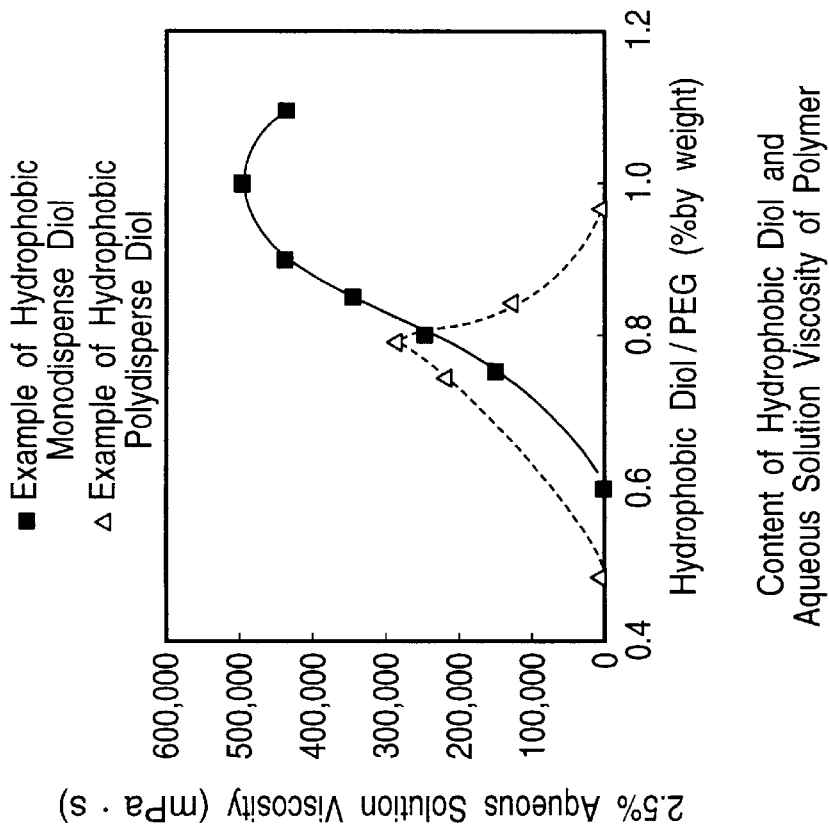
Fig. A-2
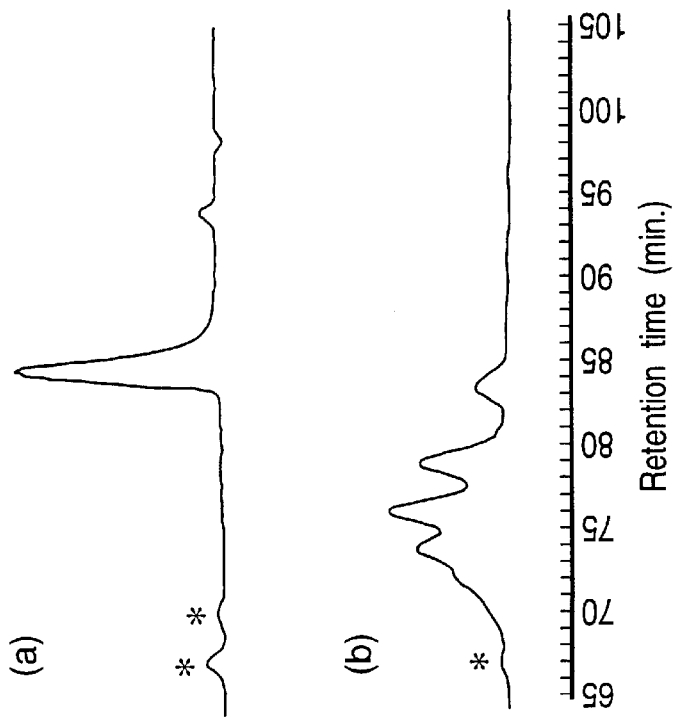
Fig. A-1
Examples of GPCs of Hydrophobic Diols
(a) Diol of Example 1  (b) Diol of Comparative Example 1
* is a ghost signal.

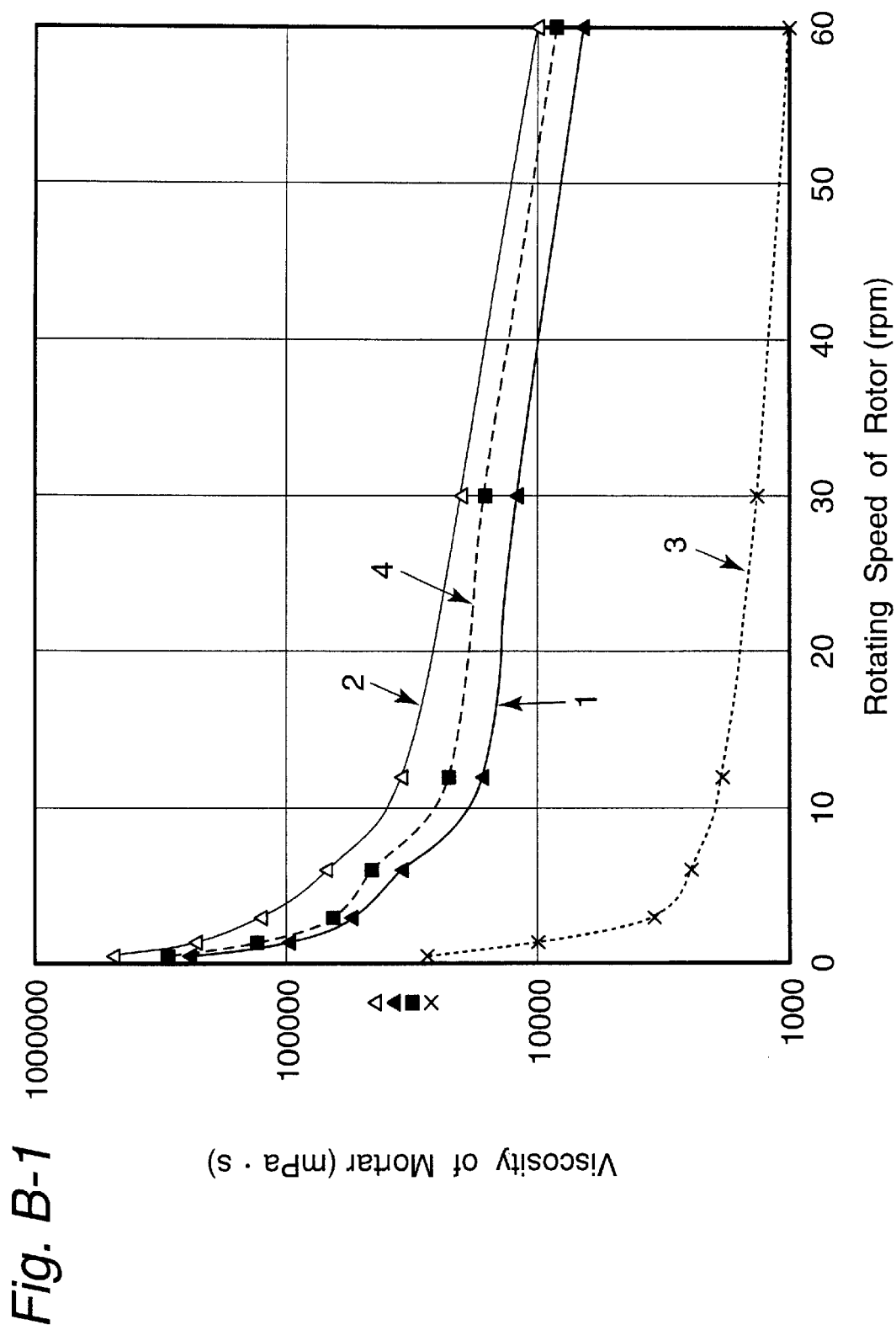
Fig. B-1

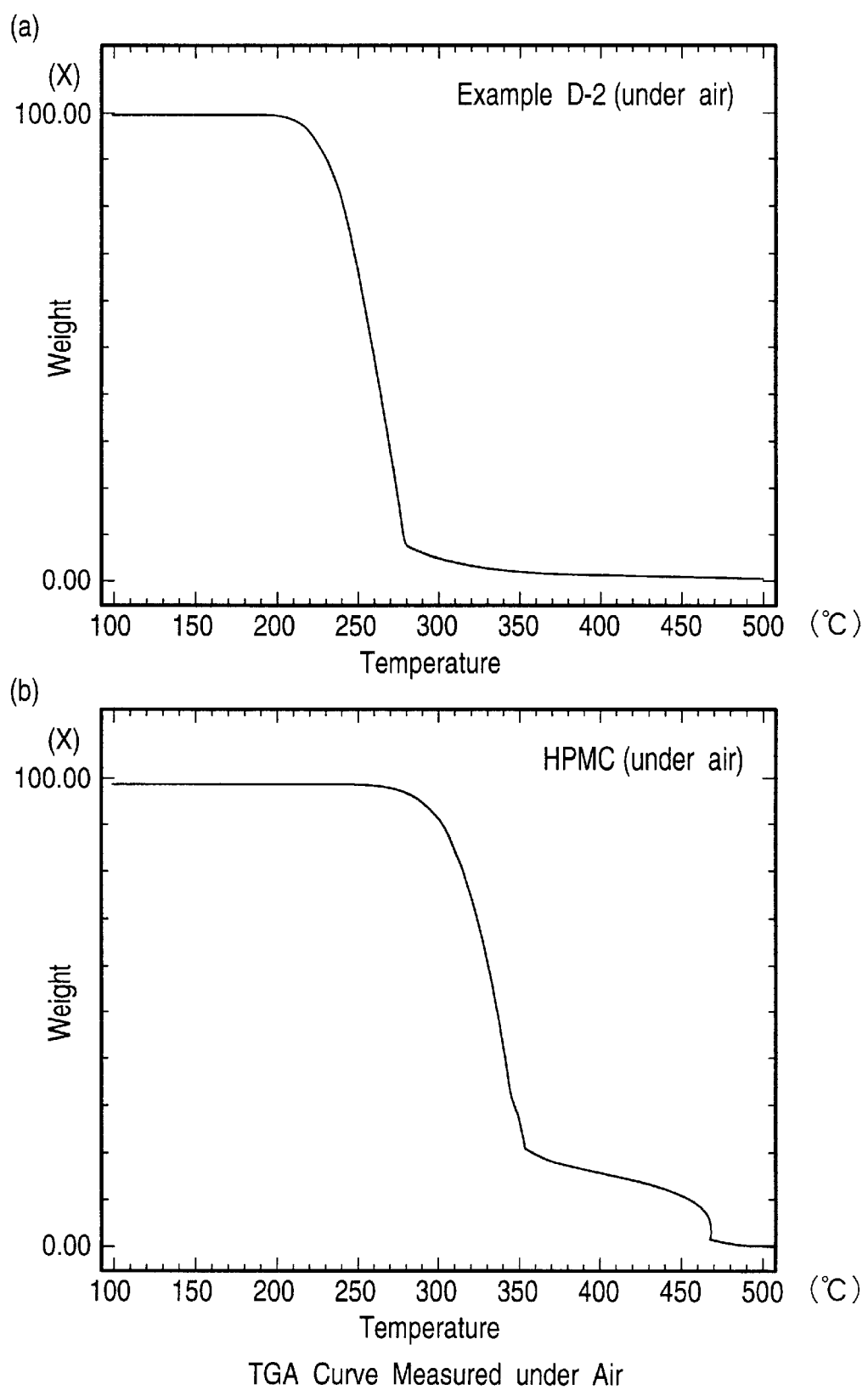
Fig. D-1
TGA Curve Measured under Air

Fig. D-2
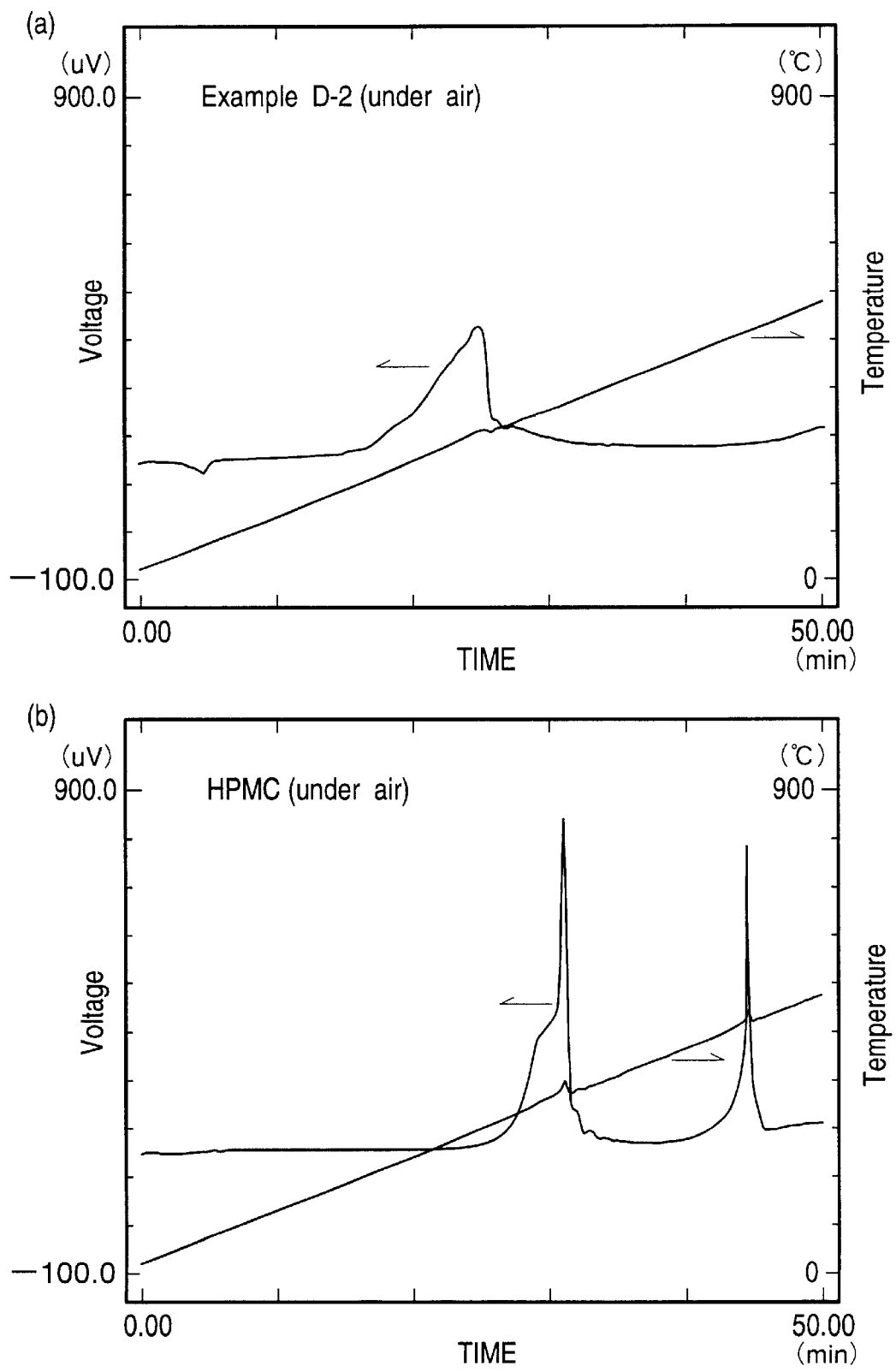
DTA Curve Measured under Air

WATER-SOLUBLE POLYURETHANE HAVING COMB-SHAPED HYDROPHOBIC GROUP AND APPLICATION THEREOF

DETAILED DESCRIPTION OF THE INVENTION

1. Technical Filed

The present invention relates to novel water-soluble polyurethane having a comb-shaped hydrophobic group.

The present invention also relates to an extruding auxiliary using the above novel water-soluble polyurethane, an extruding composition of a cement material containing the extruding auxiliary, and extruded forms of a cement material having improved strength obtained by extruding the above extruding composition of a cement material. The present invention further relates to a novel thickening agent for a mortar available for widely varying types of mortar such as repairing mortar, tile-bonding mortar, masonry mortar, spraying mortar, substrate mortar and topping mortar. The present invention further relates to a novel thickening agent for an underwater concrete and a composition for an underwater concrete containing the novel thickening agent for an underwater concrete. The present invention further relates to a novel ceramics forming binder. And the present invention further relates to a novel moisturizer for hair cosmetics excellent in moisture retention to hair.

2. Background Art

When extruding a mortar comprising a cement, a fine aggregate, a fiber and water with a vacuum extruder or the like to produce cement plates extruding the same, in order to extrude the mortar without separating water therefrom, in other words, in order to impart water retention to the mortar, there has been a need to add a water-soluble polymer to the mortar (refer to, for example, Japanese Patent Publication No. 43–7134). In order to develop sufficient water retention, the aqueous mortar solution needs to have a high viscosity, and water-soluble cellulose ethers such as methyl cellulose (MC), hydroxypropyl methyl cellulose (HPMC) and hydroxyethyl cellulose (HEC) are mainly used as the water-soluble polymer at present.

In order to retain the shape of extruded forms immediately after extrusion, in other words, in order to impart shape retention to mortar, the mortar needs to exhibit excellent thixotropic properties; and, it was not sufficient to impart shape retention thereto by an addition of only the water-soluble polymer such as methyl cellulose to the mortar. Thus, asbestos has been used in combination with water-soluble cellulose ethers (refer to, for example, Japanese Patent Publication No. 43–7134).

So, in the conventional extrusion process, the requirements of water retention and shape retention of mortar in extruding mortar have been satisfied by the use of asbestos in combination with water-soluble cellulose ethers.

In recent years, however, the harmfulness of asbestos has been pointed out and restrictions have been imposed on its use. As a result, the fibers such as various types of polymer fibers and glass fibers have become in use as substitutes for asbestos. The mortar using these asbestos-substitute fibers is, however, inferior in shape retention to the mortar using asbestos. Thus, there have been demands for the development of novel extruding auxiliary capable of imparting water retention as well as sufficient shape retention to mortar with the use of asbestos-substitute fibers.

On the other hand, the water-soluble cellulose ethers have a problem that they are likely to trap bubbles when mixing mortar, and due to the bubbles, the strength of the extruded forms of the mortar is likely to decrease.

In addition, the water-soluble cellulose ethers are relatively expensive because they are semisynthetic polymers produced from special natural wood pulp as a raw material and boost the raw material costs of the extruded forms. Furthermore, the natural wood pulp as resources is limited. Thus, a novel extruding auxiliary has been desired which can be synthesized from less expensive industrial materials.

Under those circumstances, the present inventors found an extruding auxiliary which is synthesized using polymer having a comb-shaped hydrophobic group (Japanese Patent Application Laid-Open No. 10-298261); however, the extruding auxiliary had a problem of its solubility.

The mortar having cellulose ether added thereto is not limited to the extruding mortar as described above, and various types of mortar have been used, wherein the mortars are thickened by the addition of cellulose ether thickening agents so as to improve its workability and prevent bleeding from occurring.

The cellulose ether mortar thickening agents (specifically, methyl cellulose, hydroxypropyl methyl cellulose, hydroxyethylmethyl cellulose, hydroxyethyl cellulose, hydroxyethylethyl cellulose, etc.) impart moderate thixotropic properties as well as water retention to mortar to be useful for improvement in workability (for example, making trowelling easier) and for prevention of bleeding. However, they have a disadvantage of inhibiting hydration reaction of mortar, and hence retarding curing time. This has caused problems of making curing time longer in particular under low temperature conditions (for example, outdoors in the winter) and making the mortar strength insufficient.

When placing concrete under water, it is also known that a water-soluble thickening agent is added to the concrete as an underwater anti-separating agent in order to avoid the separation of its mortar and aggregate under water (for example, Japanese Patent Application Laid-Open No. 57-123850). In order for the thickening agent to develop sufficient underwater anti-separating properties, the aqueous solution needs to have a high viscosity; thus, as the polymers for thickening agents, water-soluble cellulose ethers such as methyl cellulose (MC), hydroxypropyl methyl cellulose (HPMC), hydroxyethyl methyl cellulose (HEMC) and hydroxyethyl cellulose (HEC) are widely used at present.

The water-soluble cellulose ethers, however, have a problem of retarding the curing time of concrete (retarding setting) which may make the concrete strength easier to decrease.

Further, the water-soluble cellulose ethers have problems in terms of their costs and raw material supply since they are semisynthetic polymers, as described above. Thus, a novel thickening agent for an underwater concrete, which can be synthesized from less expensive industrial materials, has been desired.

In the forming of ceramics, particularly in extrusion of ceramics, an extrusing binder composed of a water-soluble polymer is blended so as to impart sufficient plasticity, tackiness and lubricating properties to the green sand, and various types of cellulose ethers such as methyl cellulose (MC) and hydroxypropyl methyl cellulose (HPMC) are widely used as the polymers.

The cellulose ethers, however, have a problem that their heat release in degreasing is rapid and the heat release value is high, therefore, the extruded forms are likely to be damaged at the time of degreasing. Furthermore, it is also a problem that carbonized residues or carbonized inorganic salts are likely to remain after degreasing (high carbon residue content).

Hair cosmetics such as hair conditioner, hair gel, hair foam, shampoo and rinse require moisturizer, which contains water-soluble polymer, so as to create moist feel. And, as the polymers for such cosmetics, water-soluble polymers such as polyethylene glycol (PEG) or various types of cellulose ethers are widely used at present.

However, for polyethylene glycol, it has a problem of creating a sticky hair impression, but not creating moist feel. At the same time, cellulose ethers such as hydroxyethyl cellulose (HEC) also have a problem of creating a stiffed hair impression, but not creating moist feel.

SUMMARY OF THE INVENTION

An object of the present invention is to provide novel water-soluble polyurethane having a comb-shaped hydrophobic group.

Another object of the present invention is to provide a novel extruding auxiliary to replace water-soluble cellulose ethers which is more economical, is capable of imparting excellent shape retention to mortar and excellent strength of the extruded forms of mortar, and has an improved solubility. Still another object of the invention is to provide an extruding composition of a cement material, wherein the composition has excellent shape retention, excellent strength, and is improved in solubility. Another object of the invention is to provide extruded forms of a cement material whose strength is improved.

Further object of the present invention is to provide a novel thickening agent for a mortar to replace the cellulose ether mortar thickening agents, wherein the thickening agents is available for widely varying types of mortar such as repairing mortar, tile-bonding mortar, masonry mortar, spraying mortar, substrate mortar and topping mortar.

Furthermore, an object of the present invention is to provide a novel thickening agent for an underwater concrete to replace water-soluble cellulose ethers, wherein the thickening agent is more economical and excellent in underwater anti-separating properties, and is improved in retardation of setting.

Another object of the invention is to provide a novel ceramics forming binder to replace cellulose ethers whose heat release in degreasing is slow, heat release value is low, and carbon residue content is also low.

Still another object of the present invention is to provide a novel moisturizer for a hair cosmetic to replace PEG or cellulose ethers which imparts water retention to hair and creates excellent moist hair impression.

After concentrating their energies on solving the aforementioned problems, the present inventors found novel water-soluble polyurethane having a comb-shaped hydrophobic diol as an associating group, said diol having a dispersion degree almost corresponding to a monodispersed system, which led to their completion of the present invention.

Specifically, the present invention with which can achieve the above objects is characterized as described below.

A water-soluble polyurethane according to the present invention is a polymer comprising a repeating unit (U-1) represented by the following general formula (1):

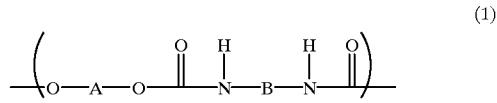

and a repeating unit (U-2) represented by the following general formula (2):

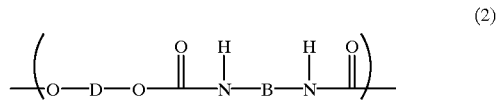

wherein a molar ratio of the repeating unit (U-1) is 0.5 or higher and 0.999 or lower, a molar ratio of the repeating unit (U-2) is 0.001 or higher and 0.5 or lower, and weight average molecular weight, as determined by gel permiation chromatography (GPC), is in the range of 10,000 to 10,000,000. In the above formula, A is a bivalent group such that HO-A-OH is water-soluble polyalkylene polyol having hydroxyl groups at least on both its ends and having a number average molecular weight of 400 to 100,000 (compound A);

B is a bivalent group such that OCN—B—NCO is a polyisocyanate compound selected from the group consisting of polyisocyanates whose total number of carbon atoms is 3 to 18 (compound B); and D is a bivalent group such that HO-D-OH is comb-shaped hydrophobic diol having the following general formula (3) (compound D):

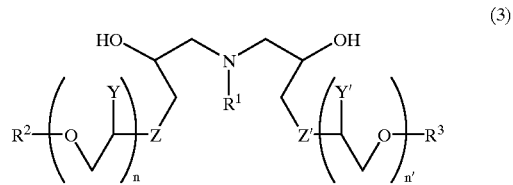

wherein $R^1$ is a hydrocarbon group or a nitrogen-containing hydrocarbon group of 1 to 20 carbon atoms; each of $R^2$ and $R^3$ is a hydrocarbon group of 4 to 21 carbon atoms; fluorine, chlorine, bromine or iodine may be substituted for part of or all of the hydrogen atoms of the hydrocarbon groups $R^1$, $R^2$ and $R^3$; $R^2$ and $R^3$ may be the same or different from each other; each of Y and Y' is hydrogen, a methyl group or a $CH_2Cl$ group; Y and Y' may be the same or different from each other; each of Z and Z' is oxygen, sulfur or a $CH_2$ group; Z and Z' may be the same or different from each other; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' may be the same or different from each other.

The molar ratio of the above repeating unit (U-1) is preferably 0.5 or higher and 0.99 or lower, the molar ratio of the above repeating unit (U-2) is preferably 0.01 or higher and 0.5 or lower, the above compound A is polyethylene glycol whose number average molecular weight is 3,000 to 20,000, the above compound B is a diisocyanate compound selected from the group consisting of aliphatic diisocyanates whose total number of carbon atoms is 3 to 18, and the water soluble polyurethane has a weight average molecular weight, as determined by GPC, in the range of 100,000 to 1,000,000.

The above compound D may be comb-shaped hydrophobic diol having the following formula (4):

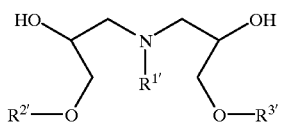

(4)

wherein $R^{1'}$ is a chain alkyl group having 4 to 18 carbon atoms, each of $R^{2'}$ and $R^{3'}$ is an alkyl group or aryl group having 4 to 18 carbon atoms, the total number of carbon atoms of $R^{1'}$, $R^{2'}$ and $R^{3'}$ is 12 to 40, and $R^{2'}$ and $R^{3'}$ are the same.

Further, the above compound D may be comb-shaped hydrophobic diol having the following formula (5):

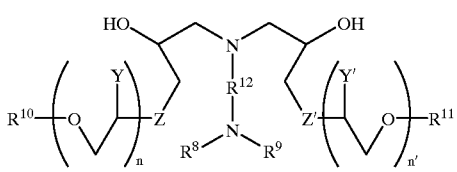

(5)

wherein $R^8$ and $R^9$ are hydrocarbon groups, the total number of carbon atoms of $R^8$ and $R^9$ being 2 to 20; $R^{10}$ and $R^{11}$ are hydrocarbon groups each of 4 to 21 carbon atoms; fluorine, chlorine, bromine or iodine may be substituted for part of or all of the hydrogen atoms of the hydrocarbon groups $R^8$, $R^9$, $R^{10}$ and $R^{11}$; $R^8$ and $R^9$ may be the same or different from each other; $R^{10}$ and $R^{11}$ may be the same or different from each other; $R^{12}$ is an alkylene group of 2 to 7 carbon atoms; each of Y and Y' is hydrogen, a methyl group or a $CH_2Cl$ group; Y and Y' may be the same or different from each other; each of Z and Z' is oxygen, sulfur or a $CH_2$ group; Z and Z' may be the same or different from each other; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' may be the same or different from each other.

The above compound B is preferably hexamethylenediisocyanate, isophoronediisocyanate, hydrogenated tolylenediisocyanate, hydrogenated xylylenediisocyanate, or norbornanediisocyanato methyl.

The extruding auxiliary for a cement material according to the present invention comprises the water-soluble polyurethane.

In the extruding auxiliary for a cement material according to the present invention, the above water-soluble polyurethane is preferably such that its 2.5% aqueous solution has a viscosity at 25° C. of 1,000 to 1,000,000 mPa·s.

The extruding composition of a cement material according to the present invention contains the above extruding auxiliary for a cement material, a hydraulic inorganic powder, a fine aggregate, a fiber and water. The fiber is preferably an asbestos-substitute fiber.

The extruded form of a cement material having improved strength according to the present invention is obtained by extruding the extruding composition of a cement material.

The thickening agent for a mortar ("a thickening agent for a mortar" is sometimes referred to as "a mortar thickening agent" hereinafter.) according to the present invention comprises the above water-soluble polyurethane.

In the mortar thickening agent according to the present invention the above water-soluble polyurethane is preferably such that the molar ratio of the above repeating unit (U-1), which has the general formula (1), is 0.5 or higher and 0.99 or lower, the molar ratio of the above repeating unit (U-2), which has the general formula (2), is 0.01 or higher and 0.5 or lower, and that its 2% aqueous solution has a viscosity in the range of 10 mPa·s to 300,000 mPa·s at 20° C.

In the mortar thickening agent according to the present invention, the above water-soluble polyalkylene polyol is preferably polyethylene glycol having a number average molecular weight of 1,000 to 20,000.

In the mortar thickening agent according to the present invention, the above polyisocyanate compound is preferably a chain aliphatic diisocyanate or an alicyclic diisocyanate. And the above polyisocyanate compound is a preferably compound selected from the group consisting of hexamethylenediisocyanate, isophoronediisocyanate, hydrogenated tolylenediisocyanate, hydrogenated xylylenediisocyanate, and norbornanediisocyanato methyl.

In the mortar thickening agent according to the present invention, the above compound D is preferably a comb-shaped hydrophobic diol represented by the following general formula (6):

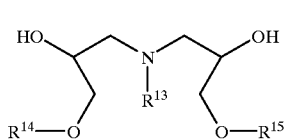

(6)

wherein $R^{13}$ is a straight-chain or chain-branched alkyl group having 4 to 18 carbon atoms, each of $R^{14}$ and $R^{15}$ is a straight-chain or branched chain alkyl group of 4 to 18 carbon atoms, and the alkyl groups $R^{14}$ and $R^{15}$ may be the same or different from each other.

The dry mortar composition according to the present invention comprises the above mortar thickening agent and a hydraulic inorganic powder.

The mortar composition according to the present invention comprises the above mortar thickening agent, a hydraulic inorganic powder and water.

A thickening agent for the underwater concrete ("a thickening agent for an underwater concrete" is sometimes referred to as "an underwater thickening agent" hereinafter.) according to the present invention comprises the above water-soluble polyurethane.

In the above underwater concrete thickening agent, the above water-soluble polyurethane is preferably such that the molar ratio of the above repeating unit (U-1), which has the general formula (1), is 0.5 or higher and 0.99 or lower, the molar ratio of the above repeating unit (U-2), which has the general formula (2), is 0.01 or higher and 0.5 or lower, and that its weight average molecular weight measured by GPC is in the range of 100,000 to 1,000,000.

In the above underwater concrete thickening agent, the above compound D is preferably a comb-shaped hydrophobic diol represented by the following formula (4):

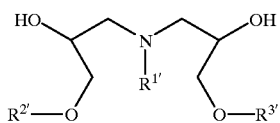

(4)

wherein $R^{1'}$ is a chain alkyl group of 4 to 18 carbon atoms, each of $R^{2'}$ and $R^{3'}$ is an alkyl group or aryl group of 4 to 18 carbon atoms, the total number of carbon atoms of $R^{1'}$, $R^{2'}$ and $R^{3'}$ is 12 to 40, and $R^{2'}$ and $R^{3'}$ are the same.

In the above underwater concrete thickening agent, the above polyisocyanate compound is preferably a chain aliphatic diisocyanate or an alicyclic diisocyanate. And the above polyisocyanate compound is preferably a compound selected from the group consisting of hexamethylenediisocyanate, isophoronediisocyanate, hydrogenated tolylenediisocyanate, hydrogenated xylylenediisocyanate, and norbornanediisocyanato methyl.

In the above underwater concrete thickening agent, 2% aqueous solution of the above water-soluble polyurethane preferably has a viscosity at 20° C. in the range of 1,000 to 500,000 mPa·s.

The composition for an underwater concrete ("a composition for an underwater concrete" is sometimes referred to as "an underwater concrete composition" hereinafter.) of the present invention is obtained by adding 0.1 to 10% by weight of the above underwater concrete thickening agent based on 100% by weight of cement.

The ceramics forming binder according to the present invention comprises the above water-soluble polyurethane.

In the above ceramics forming binder, the above water-soluble polyurethane is preferably such that the molar ratio of the above repeating unit (U-1), which has the general formula (1), is 0.5 or higher and 0.99 or lower, the molar ratio of the above repeating unit (U-2), which has the general formula (2), is 0.01 or higher and 0.5 or lower, and that its weight average molecular weight measured by GPC is in the range of 10,000 to 1,000,000.

In the above ceramics forming binder, the above water-soluble polyalkylene polyol is preferably polyethylene glycol having a number average molecular weight of 1,000 to 20,000 and the above polyisocyanate compound is chain aliphatic diisocyanate or an alicyclic diisocyanate.

For the above ceramics forming binder, preferably the above polyisocyanate compound is a compound selected from the group consisting of hexamethylenediisocyanate, isophoronediisocyanate, hydrogenated tolylenediisocyanate, hydrogenated xylylenediisocyanate, and norbornanediisocyanato methyl.

The above ceramics forming binder can be used as a binder for a ceramics extrusion.

The moisturizer for hair cosmetics according to the present invention comprises the above water-soluble polyurethane.

In the above moisturizer for hair cosmetics, the above water-soluble polyurethane is preferably such that the molar ratio of the above repeating unit (U-1), which has the general formula (1), is 0.5 or higher and 0.99 or lower, the molar ratio of the above repeating unit (U-2), which has the general formula (2), is 0.01 or higher and 0.5 or lower, and that its weight average molecular weight measured by the GPC is in the range of 10,000 to 1,000,000.

In the above moisturizer for hair cosmetics, the above water-soluble polyalkylene polyol is preferably polyethylene glycol having a number average molecular weight of 400 to 20,000 and the above polyisocyanate compound is a chain aliphatic diisocyanate or an alicyclic diisocyanate.

In the above moisturizer for hair cosmetics, the above polyisocyanate compound is preferably a compound selected from the group consisting of hexamethylenediisocyanate, isophoronediisocyanate, hydrogenated tolylenediisocyanate, hydrogenated xylylenediisocyanate and norbornanediisocyanato methyl.

BRIEF DESCRIPTION OF THE DRAWINGS

FIG. A-1 is a graph showing one example of the GPC measurements of hydrophobic diols, (a) being the GPC measurement of the diol of the example A-1; (b) being the GPC measurement of the diol of the comparative example A-1, the mark "*" representing a ghost signal.

FIG. A-2 is a graph showing the relationship between content of hydrophobic diol and aqueous solution viscosity of polymer.

FIG. B-1 is a graph showing the thickening effect of the thickening agent according to the present invention on mortar.

FIG. D-1($a$) is a graph of the TGA (thermogravimetric analysis) measurements of the binder in the invention and FIG. D-1($b$) is a graph of the TGA measurements of the currently used binder, hydroxypropyl methyl cellulose.

FIG. D-2($a$) is a graph of the DTA (differential thermal analysis) measurements of the binder in the invention and FIG. D-2($b$) is a graph of the DTA measurements of the currently used binder, hydroxypropyl methyl cellulose.

DETAILED DESCRIPTION OF THE INVENTION

The polymers obtained according to the present invention are those having a comb-shaped hydrophobic group and obtained by subjecting water-soluble polyalkylene polyols and substantially monodispersed comb-shaped hydrophobic diols to linkage with polyisocyanates.

The water-soluble polyalkylene polyols (compounds A) used in the present invention are alkylene oxide polymers having hydroxyl groups at least on both ends of their polymer chains.

The use of polyalkylene polyols having 3 or more hydroxyl groups, however, is likely to decrease the solubility of their products in water. Accordingly, polyalkylene glycols, which have primary hydroxyl groups on both ends of their polymer chains, are more preferably used.

Alkylene oxides as monomers include ethylene oxide, propylene oxide, butylene oxide and epichlorohydrin; however, in order to increase the solubility of the products in water and in polar solvent, the content of ethylene oxide is preferably 40% by weight or higher, more preferably 60% by weight or higher, and particularly preferably 70% by weight to 100% by weight. The polymerization product of ethylene oxide (polyethylene glycol, hereinafter referred to as PEG) is much more preferably used.

As the aforementioned compounds A, preferably used are those with a number average molecular weight of 400 to 100,000, more preferably 1,500 to 50,000, and much more preferably 3,000 to 20,000. When the molecular weight is in this range, a product having a high reaction rate and exhibiting sufficient aqueous solution viscosity is obtained and such a product is suitably used as thickening agents. When the molecular weight is in the range of 3,000 to 20,000, products exhibiting sufficient aqueous solution viscosity are most likely to be obtained. These suitable molecular weight ranges are particularly suitable when using the obtained water-soluble polyurethane as, for example, an extruding auxiliary and an underwater concrete thickening agent.

When using the obtained water-soluble polyurethane as a mortar thickening agent and as a ceramics forming binder, the above compounds A has a number average molecular weight of preferably 400 to 100,000, more preferably 400 to 20,000, specially preferably 1,000 to 20,000. This is because, when the molecular weight is in the range of 400 to 100,000, in mortar thickening agents, the products are most likely to be obtained which exhibit sufficient thickening properties and solubility and, in ceramics forming binders, the products are most likely to be obtained which exhibit sufficient plasticity, tackiness and solubility.

When using the obtained water-soluble polyurethane as a moisturizer for hair cosmetics, the above compound A has a number average molecular weight of preferably 400 to 100,000, more preferably 400 to 20,000, and much more preferably 1,000 to 20,000. This is because, when the molecular weight is in the above range, the products being excellent in water retention and being sufficient in solubility are obtained and such products are suitably used in hairdressings. When the number average molecular weight is in the range of 1,000 to 20,000, the products are most likely to be obtained which exhibit water retention and solubility adequate for hairdressings.

The polyisocyanate compounds (compounds B) used in the present invention are those having 3 to 18 carbon atoms (including the carbons of NCO groups) and selected from the group consisting of chain aliphatic polyisocyanates, alicyclic polyisocyanates and aromatic polyisocyanates. When the total number of carbon atoms of polyisocyanates is in this range, the solubility of the polymer obtained becomes satisfactory.

When the polyisocyanates having 3 or more NCO groups per molecule is used, however, the solubility of the products in water is likely to decrease. Accordingly, diisocyanates which have 2 NCO groups per molecule are preferably used as polyisocyanate compounds B.

In the reaction of diisocyanates with polyalkylene glycols, the reactivity of aromatic diisocyanates, chain aliphatic diisocyanates and alicyclic diisocyanates deceases in this order. However, since aromatic diisocyanate reacts so rapidly when conducting the reaction without solvent, their reaction tends to be non-uniform; thus it tends to be difficult to control the molecular weight of polyurethane.

The polymers produced by using aromatic diisocyanates may change with time in mortar which is highly basic, and their effect as an auxiliary may decrease with time after mixing. The reason may be that, since mortar is a strong alkali whose pH value is about 14, the bond, which are susceptible to alkali hydrolysis, between aromatic diisocyanates and polyalkylene glycols is broken.

In chain aliphatic diisocyanates and alicyclic diisocyanates, their carbon residue content in degreasing is low compared with an aromatic diisocyanate; accordingly, when using the obtained polymers as, for example, a binder for ceramics forming, they are more preferably used than aromatic diisocyanates.

Further, since chain aliphatic diisocyanates and alicyclic diisocyanates are less irritant than aromatic diisocyanates, they are usable for a moisturizer used in hair cosmetics.

Thus, aliphatic diisocyanates (chain aliphatic diisocyanates and alicyclic diisocyanates) having 3 to 18 carbon atoms in total are preferably used. And more preferably used are hexamethylenediisocyanate (known as HDI in a shortened form), isophoronediisocyanate (known as IPDI in a shortened form), hydrogenated xylylenediisocyanate (known as HXDI in a shortened form), hydrogenated tolylenediisocyanate (known as HTDI in a shortened form) or norbornanediisocyanatomethyl (known as NBDI in a shortened form). Of all the above, HDI is particularly preferably used.

Chain aliphatic diisocyanates are diisocyanate compounds having a structure in which the two NCO groups are linked with a straight-chain or branched chain alkylene group. They include, for example, methylenediisocyanate, ethylenediisocyanate, trimethylenediisocyanate, 1-methylethylenediisocyanate, tetramethylenediisocyanate, pentamethylenediisocyanate, 2-methylbutane-1,4-diisocyanate, hexamethylenediisocyanate (HDI), heptamethylenediisocyanate, 2,2'-dimethylpentane-1,5-diisocyanate, lysinediisocyanate methyl ester (LDI), octamethylenediisocyanate, 2,5-dimethylhexane-1,6-diisocyanate, 2,2,4-trimethylpentane-1,5-diisocyanate, nonamethyldiisocyanate, 2,4,4-trimethylhexane-1,6-diisocyanate, decamethylenediisocyanate, undecamethylenediisocyanate, dodecamethylenediisocyanate, tridecamethylenediisocyanate, tetradecamethylenediisocyanate, pentadecamethylenediisocyanate, hexadecamethylenediisocyanate, trimethylhexamethylenediisocyanate.

Alicyclic diisocyanates are diisocyanate compounds having a structure in which the two NCO groups are linked with an alkylene group having a cyclic structure. They include, for example, cyclohexane-1,2-duisocyanate, cyclohexane-1,3-duisocyanate, cyclohexane-1,4-diisocyanate, 1-methylcyclohexane-2,4-duisocyanate, 1-methylcyclohexane-2,6-duisocyanate, 1-ethylcyclohexane-2,4-diisocyanate, 4,5-dimethylcyclohexane-1,3-diisocyanate, 1,2-dimethylcyclohexane-ω,ω'-duisocyanate, 1,4-dimethylcyclohexane-ω,ω'-diisocyanate, isophoronedisocyanate (JPDI), dicyclohexylmethane-4,4'-diisocyanate, dicyclohexylmethylmethane-4,4'-diisocyanate, dicyclohexyldimethylmethane-4,4'-diisocyanate, 2,2'-dimethyldicyclohexylmethane-4,4'-diisocyanate, 3,3'-dimethyldicyclohexylmethane-4,4'-diisocyanate, 4,4'-methylene-bis(isocyanatocyclohexane), isopropylidenebis(4-cyclohexylisocyanate) (IPCI), 1,3-bis(isocyanatomethyl)cyclohexane, hydrogenated tolylenediisocyanate (HTDI), hydrogenated 4,4'-diphenylmethanediisocyanate (HMDI), hydrogenated xylylenediisocyanate (HXDI), and norbornanediisocyanatomethyl (NBDI).

Aromatic diisocyanates are diisocyanate compounds having a structure in which the two NCO groups are linked with an aromatic group such as phenylene group, alkyl-substituted phenylene group and aralkylene group or a hydrocarbon group containing an aromatic group. They include, for example, 1,3- and 1,4-phenylenediisocyanate, 1-methyl-2,4-phenylenediisocyanate (2,4-TDI), 1-methyl-2,6-phenylenediisocyanate (2,6-TDI), 1-methyl-2,5-phenylenediisocyanate, 1-methyl-3,5-phenylenediisocyanate, 1-ethyl-2,4-phenylenediisocyanate, 1-isopropyl-2,4-phenylenediisocyanate, 1,3-dimethyl-2,4-phenylenediisocyanate, 1,3-dimethyl-4,6-phenylenediisocyanate, 1,4-dimethyl-2,5-phenylenediisocyanate, m-xylenediisocyanate, diethylbenzenediisocyanate, diisopropylbenzenediisocyanate, 1-methyl-3,5- diethylbenzene-2,4-diisocyanate, 3-methyl-1,5-diethylbenzene-2,4-diisocyanate, 1,3,5-triethylbenzene-2,4-diisocyanate, naphthalin-1,4-diisocyanate, naphthalin-1,5-diisocyanate, 1-methylnaphthalin-1,5-diisocyanate, naphthalin-2,6-diisocyanate, naphthalin-2,7-diisocyanate, 1,1-dinaphthyl-2,2'-diisocyanate, biphenyl-2,4'-diisocyanate, biphenyl-4,4'-diisocyanate, 1,3-bis(1-isocyanato-1-methylethyl)benzene, 3,3'-dimethylbiphenyl-4,4'-diisocyanate, diphenylmethane-4,4'-diisocyanate (MDI), diphenylmethane-2,2'-diisocyanate, diphenylmethane-2,4'-diisocyanate and xylenediisocyanate (XDI).

The other polyisocyanates include, for example, 1,6,11-undecatriisocyanate, 1,8-diisocyanate-4-isocyanatemethyloctane and 1,3,6-hexamethylenetriisocyanate.

The comb-shaped hydrophobic diols (compounds D) used in the present invention are hydrophobic diols of substantially single component having 2 secondary hydroxyl groups and 3 hydrophobic chains per molecule and represented by the following general formula (3):

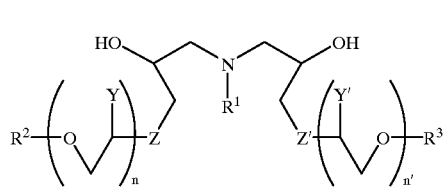

(3)

wherein $R^1$ is a hydrocarbon group such as alkyl group, alkenyl group, aralkyl group or aryl group, or a nitrogen-containing hydrocarbon group such as dialkylaminoalkyl group each having 1 to 20 carbon atoms; each of $R^2$ and $R^3$ is a hydrocarbon group, such as alkyl group, alkenyl group, aralkyl group or aryl group, having 4 to 21 carbon atoms; halogen atoms such as fluorine, chlorine, bromine or iodine may be substituted for part of or all of the hydrogen atoms of the hydrocarbon groups $R^1$, $R^2$ and $R^3$; $R^2$ and $R^3$ may be the same or different from each other, but preferably they are the same; each of Y and Y' is hydrogen, a methyl group or a $CH_2Cl$ group; Y and Y' may be the same or different from each other, but preferably they are the same; each of Z and Z' is oxygen, sulfur or a $CH_2$ group; Z and Z' may be the same or different from each other, but preferably they are the same and more preferably both of them are oxygen; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' may be the same or different from each other, but preferably they are the same.

As the compounds D having the general formula (3), preferably used are comb-shaped diols represented by the following general formula (4):

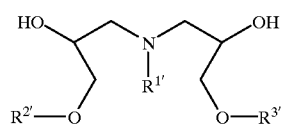

(4)

wherein $R^{1'}$ is a chain alkyl group having 4 to 18 carbon atoms, each of $R^{2'}$ and $R^{3'}$ is an alkyl group or aryl group having 4 to 18 carbon atoms, the total number of carbon atoms of $R^{1'}$, $R^{2'}$ and $R^{3'}$ is 12 to 40, and $R^{2'}$ and $R^{3'}$ are the same.

Further, as the compounds D preferably used in the present invention, comb-shaped diols having a structure represented by the following formula (5) are preferably used:

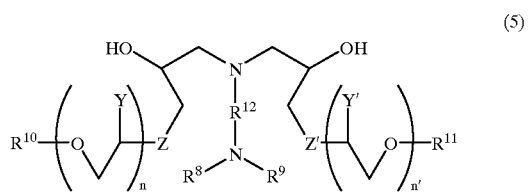

(5)

wherein $R^8$ and $R^9$ are hydrocarbon groups, the total number of carbon atoms of $R^8$ and $R^9$ being 2 to 20, preferably, $R^8$ and $R^9$ are hydrocarbon groups such as alkyl group, alkenyl group, aralkyl group or aryl group, the total number of carbon atoms being 4 to 18;

$R^{10}$ and $R^{11}$ are hydrocarbon groups each having 4 to 21 carbon atoms;

halogen atoms such as fluorine, chlorine, bromine or iodine may be substituted for part of or all of the hydrogen atoms of the hydrocarbon groups $R^8$, $R^9$, $R^{10}$ and $R^{11}$;

$R^8$ and $R^9$ may be the same or different from each other, but preferably they are the same;

$R^{10}$ and $R^{11}$ may be the same or different from each other, but preferably they are the same;

$R^{12}$ is an alkylene group having 2 to 7 carbon atoms;

Y and Y' are hydrogen, methyl groups or $CH_2Cl$ groups, Y and Y' may be the same or different from each other, but preferably they are the same;

Z and Z' are oxygen, sulfur or $CH_2$ groups, Z and Z' may be the same or different from each other, but preferably they are the same, and more preferably both of them are oxygen;

n is an integer of 0 to 15 when Z is oxygen, more preferably an integer of 0 to 5, and n is 0 when Z is sulfur or a $CH_2$ group; n' is an integer of 0 to 15 when Z' is oxygen, more preferably an integer of 0 to 5, and n is 0 when Z' is sulfur or a $CH_2$ group; and n and n' may be the same or different from each other, but preferably they are the same.

Further, as the above compounds D represented by the general formula (3) comb-shaped diols represented by the following general formula (6) are preferably used:

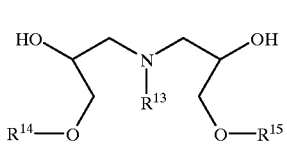

(6)

wherein $R^{13}$ is a straight-chain or branched-chain alkyl group having 4 to 18 carbon atoms; and $R^{14}$ and $R^{15}$ are straight-chain or branched-chain alkyl groups each having 4 to 18 carbon atoms, and the alkyl groups $R^{14}$ and $R^{15}$ may be the same or different from each other.

The term "substantially single component" used herein means that the compound D contains few compounds being greatly different in molecular weight. This means, in terms of degree of dispersion, that the degree of dispersion of the compounds D is about 1.00 to 1.05 and the compounds D is substantially monodispers diols. The term "degree of dispersion" used herein means a value Z shown by the following mathematical equation, if a hydrophobic diol is a mixture of k compounds, the molecular weight of its component (i) is expressed by m(i) and its molar fraction is expressed by n(i):

$$Z=\Sigma(m(i)^2 \times n(i))\div(\Sigma m(i) \times n(i))^2$$

wherein $\Sigma$ is an operator to express (i) is the sum of 1 to k, and $\Sigma n(i)=1$.

In the earlier filed application of the present inventors (Japanese Patent Application Laid-Open Publication No. 10-298261), a process is disclosed in which comb-shaped hydrophobic diols are obtained by adding a compound having an oxirane ring (oxirane compound) to low-molecular weight diols such as diethylene glycol (hereinafter referred to as spacer), as shown by the following general formula (7), in the presence of acid catalyst or alkaline catalyst:

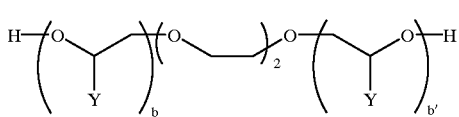

(7)

wherein b and b' are real numbers 0 or larger which satisfy the equation: (b+b')=1.5 to 6.0 and Y is a hydrophobic chain.

The hydrophobic diols obtained by the above reaction, however, are mixtures of a plurality of diols different in the sum of b and b', in other words, different in the number of hydrophobic chains. And when calculating the dispersion degree of the above hydrophobic diols, it was noticed that the dispersion degree was always considerably higher than 1.05. The reason is that, because the hydroxyl groups produced by the reaction of glycols, as spacers, with oxirane compounds further react with the oxirane compounds, diols different in the number of oxirane compounds added to the spacers are produced at the same time.

In the case where a mixture of diols, which are different in the number of oxirane compounds added to their spacers, is used as a hydrophobic diol in the production of an extruding auxiliary, when increasing the amount of the hydrophobic diol so as to obtain a polymer which imparts higher aqueous solution viscosity, the amount of the components with a large number of oxirane compounds added thereto exceeds the allowable limit of the solubility of the polymer. Thus, the use of such a hydrophobic diol gives rise to a problem that when the content of hydrophobic diol exceeds a certain critical value, the solubility of its product in water is remarkably decreased.

In light of the above problem, the present inventors concentrated their energies on seeking hydrophobic diol with a low degree of dispersion and have finally found that, when reacting 1 mol of primary amines with about 2 mols of oxirane compound having one oxirane ring and at least one hydrophobic group per molecule, the desired diol can be obtained.

In other words, the above-described comb-shaped hydrophobic diols having the general formulae (3), (4), (5) and (6) can be obtained by adding various types of oxirane-containing compounds (compounds each containing an oxirane ring) to primary amines.

As described later, various types of glycidyl ethers, 1,2-epoxy alkanes, 1,2-epoxy alkenes and glycidyl sulfide can be used as the oxirane compounds.

The addition reaction of the amino group of amines with oxirane compounds is so highly active as to progress sufficiently even without a catalyst. On the other hand, the addition reaction of the hydroxyl groups resulting from the above addition reaction with oxirane compounds is less active and hardly progresses without a catalyst such as acids and bases. Accordingly, the reaction of diols resulting from the addition reaction with oxirane compounds can be suppressed by allowing amines to react with oxirane compounds under moderate reaction conditions, for example, in the absence of catalysts.

Specifically, the primary amines include, for example, primary chain or cyclic alkylamines, primary chain or cyclic alkenylamines, primary aralkylamines, primary dialkylaminoalkylamines, primary N-benzylaminopyrrolidines, primary N-aminoalkylmorphorines, primary arylamines, primary aminopyridines and primary aminoalkylpyridines.

The primary chain alkylamines include, for example, methylamine, ethylamine, n-propylamine, isopropylamine, n-butylamine, tert-butylamine, sec-butylamine, n-pentylamine, n-hexylamine, n-heptylamine, 2-aminoheptane, n-octylamine, isooctylamine, 2-aminooctane, 2-ethylhexylamine, 2-amino-6-methylheptane, nonylamine, isononylamine, 1,4-dimethylheptylamine, 3-aminononane, 2-amino-6-ethylheptane, n-decylamine, n-undecylamine, 2-aminoundecane, 6-aminoundecane, n-dodecylamine, n-tridecylamine, 2-aminotridecane, n-tetradecylamine, 2-aminotetradecane, n-pentadecylamine, 8-aminopentadecane, n-hexadecylamine, n-heptadecylamine, n-octadecylamine, n-nonadecylamine and 2-aminononadecane.

The primary chain alkenylamines include, for example, allylamine and oleylamine.

The primary cyclic alkylamines include, for example, cyclohexylamine, cycloheptylamine, 2-methylcyclohexylamine, 3-methylcyclohexylamine, 4-methylcyclohexylamine, aminomethylcyclohexane, cyclooctylamine, 2,3-dimethylcyclohexylamine, 3,3,5-trimethylcyclohexylamine, 4-tert-butylcyclohexylamine, 1-cyclopentyl-2-aminopropane, 1-aminoindan, cyclododecylamine, o-aminobicyclohexyl, 3-aminospiro[5,5]undecane, bornylamine, 1-adamantaneamine, 2-aminonorbornane and 1-adamantanemethylamine.

The primary cyclic alkenylamines include, for example, dihydroabiethylamine and 2-(1-cyclohexenyl)ethylamine.

The primary aralkylamines include, for example, benzylamine, phenethylamine, p-methoxyphenethylamine, α-phenylethylamine, 1-methoxy-3-phenylpropylamine and N-aminopropylaniline.

The primary dialkylaminoalkylamines include, for example, N,N-dimethylethylenediamine, N,N-diethylethylenediamine, N,N-diisopropylethylenediamine, N,N-dimethyl-1,3-propanediamine, N,N-diethyl-1,3-propanediamine, diethylaminopropylamine, dibutylaminopropylamine, 1-dimethylamino-2-propylamine, N2,N2-dimethyl-1,2-propanediamine, 4-dimethylaminobutylamine, 1-dimethylaminoethyl-2-aminopropane, N,N-dimethylneopentanediamine, 1-diethylamino-2-propylamine, 6-dimethylaminohexylamine, 2-di-n-propylaminoethylamine, N-ethyl-N-butylethylenediamine, 7-diethylaminoheptylamine, N1,N1-di-n-propyl-1,2- propanediamine, N',N'-di-n-propanediamine, 5-diethylaminopentylamine, 2-amino-5-diethylaminopentane, N,N-di-n-butylethylenediamine, N,N-di-tert-butylethylenediamine, 2-diisobutylaminoethylamine, 4-diisopropylaminobutylamine, 7-diethylaminoheptylamine, 3-(di-n-butylamino)propylamine, N,N-diisobutyl-1,6-hexanediamine, 3-dioctylaminopropylamine, 3-didecylaminopropylamine, 1-(2-aminoethyl)piperidine, 3-piperidinopropylamine, 4-pyrrolidinobutylamine, N-aminoethyl-4-pipecoline, 3-aminotropane, 5-pyrrolidinoamylamine, N-aminopropyl-4-pipecoline, 1-(3-aminopropyl)-2-pipecoline, 1-azabicyclo[2.2.2]octo-3-ylamine, 1-benzyl-3-aminopyrrolidine and N1-ethyl-N1-phenylpropane-1,3-diamine.

The primary N-benzylaminopyrrolidines include, for example, N-benzyl-3-aminopyrrolidine and N-benzyl-2-methyl-3-aminopyrrolidine.

The primary N-aminoalkylmorphorines include, for example, N-aminoethylmorphorine and N-aminopropylmorphorine.

The primary arylamines include, for example, aniline, 2-chloroaniline, 2,3-dichloroaniline, 2,4-dibromoaniline, 2,4,6-tribromoaniline, o-toluidine, 2-chloro-4-methylaniline, 2,3-dimethylaniline, 2,4-dimethylaniline, 2,5-dimethylaniline, 2-ethylaniline, 2-isopropylaniline, 4-tert-butylaniline, p-decylaniline, p-dodecylaniline, p-tetradecylaniline, 4-cyclohexylaniline, 2-aminobiphenyl, 1-naphthylamine, 5-aminoindan, 1-aminonaphthacene, 6-aminochrysene and 1-aminopyrene.

The primary aminopyridines include, for example, 2-amino-3-methylpyridine, 2-amino-4-methylpyridine, 2-amino-6-methylpyridine, 2-amino-4-ethylpyridine, 2-amino-4-propylpyridine, 2-amino-4,6-dimethylpyridine and 2-amino-3-nitropyridine.

The primary aminoalkylpyridines include, for example, 2-aminomethylpyridine, 3-aminomethylpyridine, 4-aminomethylpyridine and 3-aminomethyl-6-chloropyridine.

The other primary amines include, for example, pyrazines such as 2-aminomethylpyrazine, 2-aminopyrazine and sulfurene.

As the oxirane compounds, various types of glycidyl ethers, 1,2-epoxy alkanes, 1,2-epoxy alkenes and glycidyl sulfides can be used.

The glycidyl ethers include, for example, alkylglycidyl ethers, alkenylglycidyl ethers, aralkylglycidyl ethers and arylglycidyl ethers.

The alkylglycidyl ethers include, for example, n-butylglycidyl ether, sec-butylglycidyl ether, tert-butylglycidyl ether, glycidylpentyl ether, glycidylhexyl ether, glycidyloctyl ether, 2-ethylhexylglycidyl ether, 2-methyloctylglycidyl ether, glycidylnonyl ether, decylglycidyl ether, dodecylglycidyl ether, glycidyllauryl ether, glycidyltridecyl ether, glycidyltetradecyl ether, glycidylpentadecyl ether, glycidylhexadecyl ether, glycidylstearyl ether, 3-(2-(perfluorohexyl)ethoxy)-1,2-epoxypropane, and 3-(3-perfluorooctyl-2-iodopropoxy)-1,2-epoxypropane.

The alkenylglycidyl ethers include, for example, allylglycidyl ether and oleylglycidyl ether.

The aralkylglycidyl ethers include, for example, benzylglycidyl ether and phenetylglycidyl ether.

The arylglycidyl ethers include, for example, phenylglycidyl ether, 4-tert-butylphenylglycidyl ether, 2-ethylphenylglycidyl ether, 4-ethylphenylglycidyl ether, 2-methylphenylglycidyl ether, glycidyl-4-nonylphenyl ether, glycidyl-3-(pentadecadienyl)phenyl ether, 2-bisphenylglycidyl ether, benzylglycidyl ether, α-naphthylglycidyl ether and dibromophenylglycidyl ether.

The other glycidyl ethers include the glycideyl ethers represented by the following formula 8, for example, glycidyl ethers of adducts of alcohols and phenols with alkylene oxides (ethylene oxide adducts, propylene oxide adducts, epichlorohydrin adducts, etc.);

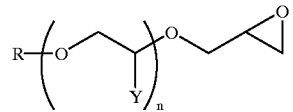

(8)

wherein R is an alkyl group or aryl group; Y is hydrogen, a methyl group or CH$_2$C' group; n is an integer of 1 to 15. The glycidyl ethers of ethylene oxide adducts are, for example, glycidyl ethers of 2-ethylhexylalcohol—ethylene oxide adduct, of lauryl alcohol—ethylene oxide adduct, of 4-tert-butylphenol—ethylene oxide adduct and of nonylphenol—ethylene oxide adduct.

In addition, the glycidyl ethers which are adducts of alcohols and phenols with propylene oxide, with propylene oxide/ethylene oxide, and with epichlorohydrin can also be used. Although the glycidyl ethers as industrial chemicals usually include glycidyl ethers of epichlorohydrin adducts as by-products, such raw materials of low purity can be used, either. The number of adducts n is suitably about 1 to 15, in terms of the aqueous solution viscosity of polyurethane.

The 1,2-epoxyalkanes and 1,2-epoxyalkenes include, for example, 1,2-epoxyhexane, 1,2-epoxyheptane, 1,2-epoxyoctane, 1,2-epoxynonane, 1,2-epoxydecane, 1,2-epoxydodecane, 1,2-epoxytetradecane, 1,2-epoxyhexadecane, 1,2-epoxyoctadecane, 1,2-epoxyeicosane, 1,2-epoxy-7-octene and 1,2-epoxy-9-decene.

The other oxirane compounds include, for example, alkylglycidyl thioethers (alkylglycidylsulfides), such as 2-ethylhexylglycidyl sulfide and decylglycidyl sulfide, and arylglycidyl thioethers (arylglycidyl sulfides) such as p-nonylphenylglycidyl sulfide.

The compounds D can be obtained by reacting the above amines with the above oxirane compounds in the ratio of 1 molecule of the amines to 2 molecules of the oxirane compounds. The reaction formula (9) is as follows:

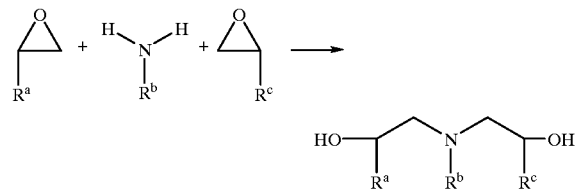

(9)

wherein $R^a$, $R^b$ and $R^c$ correspond to the substituents of the above-described general formulae (3), (4), (5) and (6).

When using the glycidyl ethers as the oxirane compound, the reaction is facilitated much more than when using 1,2-epoxyalkanes, 1,2-epoxyalkenes or glycidyl sulfides. This may be because the glycidyl ethers are highly reactive with the amines.

The compounds D have 3 hydrophobic chains per molecule, and allowing these hydrophobic chains to be adjacent to each other facilitates effectively the hydrophobic association among water-soluble polyurethane in aqueous solution. Each hydrophobic chain needs to have as many carbon atoms as it can have a length enough to allow the polymer to form satisfactory association. The number of carbon atoms of the amines is preferably 1 or larger and 20 or smaller. The use of the amines whose number of carbon atoms is in the above range prevents the solubility of polyurethane from decreasing. More preferably used are the chain or cyclic alkyl amines whose number of carbon atoms is 1 to 18 carbon atoms, and much more preferably the chain alkyl amines whose number of carbon atoms is 4 to 18.

The number of carbon atoms of the hydrophobic groups contained in the glycidyl ethers is preferably 4 or larger and 21 or smaller. The use of the glycidyl ethers whose hydrophobic groups have carbon atoms in the above range allows the aqueous solution viscosity of the polyurethane to be satisfactorily high and prevents the solubility of the polyurethane from decreasing. More preferably used are the alkylglycidyl ethers having straight-chain alkyl groups or branched chain alkyl groups whose number of carbon atoms is 4 to 18 as the hydrophobic groups or the arylglycidyl ethers having aromatic groups or alkyl-substituted aromatic groups whose number of carbon atoms is 6 to 18 as the hydrophobic groups.

For the same reason, the number of carbon atoms of the hydrophobic groups contained in the 1,2-epoxyalkanes, 1,2-epoxyalkenes, alkylglycidyl thioethers and arylglycidyl thioethers are preferably 4 or larger and 21 or smaller.

The larger the total number of carbon atoms of the three hydrophobic chains (the total number of carbon atoms of the substituents $R^1$, $R^2$ and $R^3$ each having the above-mentioned general formula (3), the total number of carbon atoms of the substituents $R^{1'}$, $R^{2'}$ and $R^{3'}$ each having the above-mentioned general formula (4), the total number of carbon atoms of the substituents $R^8$, $R^9$, $R^{10}$ and $R^{11}$ each having the above-mentioned general formula (5), and the total number of carbon atoms of the substituents $R^{13}$, $R^{14}$ and $R^{15}$ each having the above-mentioned general formula (6)) is, the more the polymers are likely to associate in water, therefore, the higher aqueous solution viscosity can be obtained. However, too large a total number of carbon atoms is likely to allow the solubility of the polymers in water to decrease. The total number of carbon atoms of the hydrophobic groups is preferably in the range of 12 to 40, more preferably in the range of 12 to 34, and much more preferably in the range of 12 to 24. The use of the glycidyl ethers whose hydrophobic groups have carbon atoms in the above range allows the aqueous solution viscosity of the polymers obtained to be satisfactorily high and prevents the solubility of the polyurethane in water from decreasing.

The process of preparing comb-shaped hydrophobic diols will be described below; however, it should be understood that the present invention is not intended to be limited to this specific synthetic process.

Amine and an oxirane compound, as raw materials, are prepared in a reactor equipped with a stirring apparatus, a raw material introducing mechanism and a temperature controlling mechanism and are reacted with each other at a predetermined reaction temperature while being stirred.

The reaction can be conducted without a solvent; however, commonly used solvents such as dimethylformamide (DMF) may be used.

In regard to the introduction of raw materials, the amine and the oxirane compound may be prepared at a time, or either of the amine and the oxirane compound may be prepared in the reactor first, then the rest may be introduced continuously or by steps.

The suitable reaction temperature is room temperature to about 160° C., more preferably 60° C. to 120° C.

The reaction time is about 0.5 to 10 hours, though it depends on the reaction temperature.

The dispersion degree of the diol obtained after completion of the reaction can be measured by the GPC.

The OH value can be obtained by conventional procedure.

The water-soluble polyurethane having a comb-shaped hydrophobic group is synthesized by the reaction of the two hydroxyl groups of polyalkylene glycol (compound A) and comb-shaped hydrophobic diol (compound D) with the two NCO groups of diisocyanate compound (compound B), as shown by the following general formula (10):

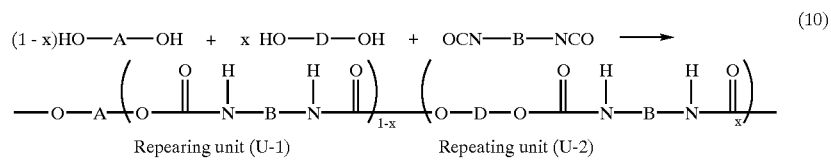

The water-soluble polyurethane whose repeating unit (U-1) has a molar ratio of (1-x) and whose repeating unit (U-2) has a molar ratio of x is obtained by conducting the above reaction at compound A to compound D molar ratio of (1-x): x.

Now the process of producing the water-soluble polyurethane will be described while giving an example; however, it should be understood that the present invention is not intended to be limited to the specific example.

The contents of a reactor equipped with a stirring apparatus, a raw material introducing mechanism and a temperature controlling mechanism is replaced with an inert gas, first. Polyalkylene glycol is prepared in the reactor. According to the situation, a solvent is also prepared in the reactor.

A catalyst is added while controlling the temperature of the reactor at a set reaction temperature. A diisocyanate compound and comb-shaped hydrophobic diol are introduced into the reactor while stirring the contents of the reactor. The way of introducing them is not limited to any specific one. They may be introduced continuously or intermittently. And the diisocyanate compound and comb-shaped hydrophobic diol may be introduced at a time or may be introduced one at a time in this order or in reverse order.

The catalyst is not necessarily added to the polyalkylene glycol before the reaction. It is possible to add the catalyst after adding the diisocyanate compound and comb-shaped hydrophobic diol to the polyalkylene glycol and then start the reaction. Alternatively it is possible to add the catalyst to the diisocyanate compound and comb-shaped hydrophobic diol previously, add these to the polyalkylene glycol, and then start the reaction.

After the set reaction time, the product is taken from the reactor and processed to finished goods in the form of pellets, flakes, powder or solution.

The catalyst used in the reaction is not limited to any specific one, the known catalysts, such as organic metal compounds, metal salts, tertiary amines, and other basic catalysts and acid catalysts, which are commonly used in the reaction of isocyanates with polyols can also be used. Those catalysts include, for example, dibutyltin dilaurate (hereinafter referred to as DBTDL for short), dibutyltin di(dodecilthiolate), tin octanoate, phenylmercury acetate, zinc octoate, lead octoate, zinc naphthenate, lead naphthenate, triethylamine (TEA), tetramethylbutanediamine (TMBDA), N-ethyl morpholine (NEM), 1,4-diaza[2.2.2]bicyclooctane (DABCO), 1,8-diazabicyclo[5.4.0]-7-undecene (DBU) and N,N'-dimethyl-1,4-diazacyclohexane (DMP) Of all the above DBTDL is preferably used.

The amount of catalyst used in the reaction varies depending on the reaction temperature and type of catalyst and is not limited to any specific amount. 0.0001 to 0.1 mol of catalyst is sufficient for 1 mol of polyalkylene glycol, more preferably about 0.001 to 0.1 mol of catalyst is used for 1 mol of polyalkylene glycol.

The reaction can be conducted without a solvent; however, it can also be conducted with a solvent so as to decrease the melting viscosity of the product. As a solvent, the solvents having no active hydrogen are effectively used. Those solvents include, for example, halogen solvents such as carbon tetrachloride, dichloromethane, chloroform and trichlene; aromatic solvents such as xylene, toluene and benzene; saturated hydrocarbon solvents such as decane, octane, heptane, hexane, cyclohexane and pentane; ether solvents such as dioxane, tetrahydrofuran, diethyl ether, dimethyl ether and ethylene glycol dimethyl ether; ketone solvents such as diethyl ketone, methyl ethyl ketone and dimethyl ketone; and ester solvents such as ethyl acetate and methyl acetate.

The process to conduct the reaction without a solvent is advantageous in terms of production costs, since it does not require the step of desolvation. And such a process is preferably used, since it is unlikely to cause environmental pollution.

The amount of diisocyanate compound used in the reaction varies a little depending on the application of the polymer obtained. When using the obtained polymer in, for example, extruding auxiliary and underwater concrete thickening agent applications, the molar ratio of the NCO groups of the diisocyanate compound to the total number of the OH groups of each of polyalkylene glycol and comb-shaped hydrophobic diol (NCO/OH) is preferably 0.8 to 1.3, more preferably 0.9 to 1.2, much more preferably 1.0 to 1.1. When the molar ratio (NCO/OH) is in the range of 0.8 to 1.3, the product can have a sufficiently large average molecular weight and its ability as an extruding auxiliary or underwater concrete thickening agent becomes satisfactory.

When using the product in the mortar thickening agent applications, the molar ratio of the NCO groups of the diisocyanate compound to the total number of the OH groups of each of polyalkylene glycol and comb-shaped hydrophobic diol (NCO/OH) is preferably 0.7 to 1.3, more preferably 0.8 to 1.05, much more preferably 0.9 to 1.00. When the molar ratio (NCO/OH) is in the range of 0.7 to 1.3, the product can have a satisfactorily large average molecular weight, its ability as a thickening agent becomes satisfactory, and its decrease in solubility due to the crosslinking reaction does not occur.

When using the product in the applications such as ceramics forming binder and moisturizer for use in hair cosmetics, the molar ratio of the NCO groups of the diisocyanate compound to the total number of the OH groups of each of polyalkylene glycol and comb-shaped hydrophobic diol (NCO/OH) is preferably 0.7 to 1.3, more preferably 0.8 to 1.2. When the molar ratio (NCO/OH) is in the range of 0.7 to 1.3, the product can have a satisfactorily large average molecular weight and its ability as a ceramics forming binder and a moisturizer for hair cosmetics becomes satisfactory.

Under the conditions that the number of moles of diisocyanate and the total number of moles of polyalkylene glycol and comb-shaped hydrophobic diol are almost the same, the product having the largest molecular weight is obtained.

However, when polyalkylene glycol and comb-shaped hydrophobic diol contain water, an excess of diisocyanate needs to be used for making up for the diisocyanate having been decomposed by water. Accordingly, a fully dried raw material is preferably used. The water content of the raw material is preferably 5,000 ppm or lower, more preferably 1,000 ppm or lower, and much more preferably 200 ppm or lower.

For the amount of comb-shaped hydrophobic diol used in the reaction, generally 0.001 to 1 mol of comb-shaped hydrophobic diol is suitably used for 1 mol of polyalkylene glycol (x is 0.001 to 0.5), though it varies depending on the molecular weight of the polyalkylene glycol and the number of carbon atoms contained in the hydrophobic groups of the comb-shaped hydrophobic diol. When the number of moles of the comb-shaped hydrophobic diol is in this range, a product is obtained which has a desired thickening effect and has its solubility satisfactorily maintained. The values in parenthesis indicates the value x in the above-described general formula (10).

When using the product in the applications such as mortar thickening agent, underwater concrete thickening agent, ceramics forming binder and moisturizer for use in hair cosmetics, 0.01 to 1 mol of comb-shaped hydrophobic diol is suitably used for 1 mol of polyalkylene glycol (x is 0.01 to 0.5). When the number of moles of the comb-shaped hydrophobic diol is in this range, the product has a sufficient thickening effect needed for a mortar thickening agent etc. or a sufficient hydrophobic nature needed for an underwater concrete thickening agent, a ceramics forming binder, a moisturizer for hair cosmetics and has its solubility satisfactorily maintained. The values in parenthesis indicates the value x in the above-described general formula (10).

As described above, when using polyethylene glycol with a number average molecular weight of 3,000 to 20,000 as polyalkylene glycol, the most excellent polyurethane as an extruding auxiliary, an underwater concrete thickening agent, etc. is likely to be produced. In this case, the amount of comb-shaped hydrophobic diol used in the reaction is preferably 0.01 to 1 mol for 1 mol of polyethylene glycol (x is 0.01 to 0.5), more preferably 0.03 to 0.67 mol (x is 0.03 to 0.4). When the amount of the comb-shaped hydrophobic diol is in this range, a product has a satisfactory effect as an extruding auxiliary, an underwater concrete thickening agent.

The suitable reaction temperature varies depending on the type and amount of the catalyst used; however, it is preferably in the range of 50 to 180° C., more preferably in the range of 60 to 150° C., and much more preferably in the range of 80 to 120° C. When the reaction temperature is in the range of 50 to 180° C., the reaction rate is sufficiently high, therefore, the production is economical; in addition, the product is not subjected to thermal decomposition.

The reaction time varies depending on the type and amount of the catalyst used, and it is not limited to any specific time. A product can be obtained satisfactorily when the reaction time is 1 minute to 10 hours.

The reaction pressure is not limited to any specific pressure. The reaction can be conducted at normal pressures, reduced pressures and increased pressures. The reaction is preferably conducted at normal pressures or slightly increased pressures.

The product obtained after the completion of the reaction can be subsequently subjected to grinding process, if necessary. In this case, the product obtained by the reaction is taken from the reactor and ground into particles of suitable diameter, for example, of diameter not more than 1 mm. For the grinding, apparatus commonly used for grinding polymers having a relatively low melting point, such as freeze grinder, impact grinder and grinding-type crusher.

Now the characteristics of water-soluble polyurethane obtained according to the present invention will be described below.

According to the present invention, there is obtained water-soluble polyurethane whose 2.5% aqueous solution viscosity (the viscosity of polyurethane aqueous solution whose polyurethane concentration is 2.5% by weight is measured with B type rotating viscometer at 6 rpm at 25° C.) is about 100 mPa·s to 1,000,000 mPa·s or higher.

The weight average weight molecular of the polymer obtained according to the present invention is in the range of about 10,000 to 10,000,000.

The water-soluble polyurethane can be used in the solid flake state, or in the aqueous solution or alcohol dilute solution states.

Since the water-soluble polyurethane according to the present invention is excellent in viscosity characteristics, solubility in water or in polar solvents, moisture retention, etc., it can be suitably used as an extruding auxiliary for cement materials, a mortar thickening agent, an underwater concrete thickening agent, a ceramics forming binder and a moisturizer for hair cosmetics, as described below. However, those skilled in the art will easily recognize that the present invention is not limited in its application to the above examples and it can be used in the other various applications, either, because of its characteristics.

Extruding Auxiliary

The above-described water-soluble polyurethane according to the present invention is suitably used as an extruding auxiliary for use in a cement material.

As described above, the water-soluble polyurethane according to the present invention is allowed to have a viscosity of a 2.5% aqueous solution at 25° C. (a 2.5% aqueous solution viscosity at 25° C.) of about 100 to 1,000,000 mPa·s; however, when using it as, in particular, an extruding auxiliary for a cement material, it has a 2.5% aqueous solution viscosity at 25° C. (a 2.5% aqueous solution viscosity at 25° C.) of preferably 1,000 to 1,000,000 mPa·s, and more preferably 10,000 to 500,000 mPa·s. For the water-soluble polyurethane having a 2.5% aqueous solution viscosity at 25° C. of about 1,000 to 1,000,000 mPa·s, when being used as an extruding auxiliary, it hardly permits water to separate from the cement material during extrusion since it has a satisfactory water retention, it imparts a moderate tackiness to the material, and it allows the surface of the extruded forms to be kept satisfactorily smooth.

When mixing 40 parts by weight of polymer aqueous solution whose polymer concentration is 2.5% and 100 parts by weight of cement, the ratio of the polymer to the cement becomes 1% by weight and the ratio of water to the cement becomes 40% by weight, and these ratios are typical for extrusion mortar, as described later. Accordingly, in order to define the characteristics of an extruding auxiliary, its 2.5% aqueous solution viscosity is suitably used.

For the polyurethane according to the present invention, its weight average molecular weight measured by the GPC is preferably in the range of 100,000 to 1,000,000 when being used as an extruding auxiliary. In the GPC, chloroform solution was used. And the molecular weight was obtained by calibrating the measurements using standard polystyrene as a standard reference material. When the polyurethane has a weight average molecular weight of in this range, it is suitable to be an extruding auxiliary, because its aqueous solution viscosity is satisfactory and its solution does not show stringiness.

When being used as an extruding auxiliary, the above polyurethane is more preferably in the powder state, in terms of handlability. The powder of particle diameter 16 mesh (1 mm) or less is preferably used. The reason is that the powder of particle diameter 16 mesh (1 mm) or less exhibits a satisfactory solubility.

The above extruding auxiliary may contain an anti-oxidant, a stabilizer, a plasticizer, a diluent, an anti-caking agent, grinding auxiliary, etc. besides the above water-soluble polyurethane as a chief ingredient.

Extruding Composition of a Cement Material

As the extruding compositions of a cement material used in the present invention, the compositions equivalent to the known extruding compositions of a cement material are effectively used, provided that those compositions contain the extruding auxiliaries according to the present invention instead of cellulose ethers, such as methyl cellulose and hydroxypropyl methyl cellulose, which have been used as an extruding auxiliary.

Specifically, the extruding compositions of ca ement material used in the present invention contain hydraulic powder, such as normal portland cement, special portland cement, portland blastfurnace slag cement, portland fly-ash cement, high alumina cement and plaster, as a chief ingredient, fine aggregates, fiber, water and extruding auxiliaries.

Although extrusion can be carried out without a fine aggregate, it is usually used so as to improve the accuracy for dimensions of extruded forms and reduce the raw material costs. As a fine aggregate, sand is mostly used; however, light-weight aggregates such as pearlite, vermiculite, shirasu balloon, pumice, shattered foamed concrete and shattered foamed plastics can be used, as well.

Fibers are added so as to improve the shape retention of the compositions (mortar). As the fiber preferably used are various types of fibers such as asbestos, rock wool, glass fiber, carbon fiber and polymer fibers. In terms of safety, fibers other than asbestos (hereinafter abbreviated as asbestos-substitute fibers), such as rock wool, glass fiber, carbon fiber and polymer fiber (polypropylene fiber, Vinylon fiber, aramid fiber, etc.) are more preferably used.

The compositions may contain, for example, inorganic materials such as fly ash, silica fume, bentonite and clay; pulp; water absorbing agents such as water absorbing resin; reemulsified resin powder; various types of water reducing agents; surfactants; and anti-foaming agents.

The amount of the extruding auxiliary of the present invention added varies depending on the composition of the mortar; however, the amount is usually about 0.1 to 5% by weight per 100% by weight of hydraulic powder contained in the extruding cement compositions for building material, more preferably 0.2 to 3% by weight, and much more preferably 0.5 to 1.5% by weight. When the amount of the extruding auxiliary added is in the range of 0.1 to 5% by weight, the extruding auxiliary works effectively, the compositions develop a moderate tackiness, and satisfactory results are obtained in terms of productivity. The optimum amount varies depending on the concrete extrusion conditions such as composition of extrusion compositions, performance of extruder and shape of extruded forms; however, generally satisfactory results are obtained when adding the extruding auxiliary in an amount 50 to 95% by weight of the cellulose ethers having been added in the conventional compositions. The method of adding the extruding auxiliary may be such that the extruding auxiliary in the dried flake or dried powder state and the other ingredients of the cement compositions are mixed while stirring or such that first the aqueous solution of the extruding auxiliary is made and the solution is added to the other ingredients of the cement composition.

It goes without saying that the extruding auxiliary of the present invention can be used as the extruding auxiliary in combination with the currently used thickening agents such as cellulose ethers, polyacrylamide polymers, polyethylene oxides and polyvinyl alcohols.

The ratio of water contained in the above composition varies depending on the type and amount of the fine aggregate and fiber used; however, the suitable weight ratio of water to hydraulic powders, such as cement, (water-cement ratio) is preferably in the range of 0.2 to 1, more preferably preferably in the range of 0.3 to 0.7, and much more preferably 0.3 to 0.4. When the water-cement ratio is in the range of 0.2 to 1, the water content required for the hydration of the cement becomes moderate, and extruded forms of high flexural strength are obtained. In order to obtain extruded forms of high strength, the water-cement ratio is more preferably in the range of 0.3 to 0.7, and much more preferably in the range of 0.3 to 0.4. When the water-cement ratio is in the range of 0.3 to 0.4, the extruded forms of the highest strength are likely to be produced.

The amount of fine aggregate added to the compositions may be almost the same as that of the aggregate added to the conventional extrusion mortar; typically, the amount of fine aggregate, such as sand, added to the compositions is preferably about 10 to 500% by weight per 100% by weight of hydraulic powders, and more preferably 30 to 300% by weight.

The amount, of fiber added to the compositions varies depending on the shape of extruded forms to be obtained; however, one of the advantages of using the extruding auxiliary of the present invention is, for example, that the addition of fiber even in an amount smaller than that of the conventional extrusion allows the mortar to have a sufficient shape retention. When using asbestos as a fiber, the amount of the asbestos used in the compositions may be decreased to about 70 to 95% of that of the conventional mortar. The use of asbestos-substitute fibers such as polymer fibers is much more effective in decreasing the amount of fiber used in the compositions. It allows the amount of fiber to be decreased to about 50 to 90% of that of the conventional mortar. The reason why the use of asbestos-substitute fibers is much more effective in decreasing the amount of fibers used in the compositions is that asbestos-substitute fibers are inferior to asbestos in shape retention. The lack of shape retention of those fibers can be supplemented with the extruding auxiliary of the present invention. Typically, the amount of fiber added to the compositions is preferably about 0.1 to 10% by weight per 100% by weight of hydraulic powders added to the same, more preferably 0.5 to 5% by weight.

These cement material compositions can be extruded in the conventional manner, that is, in such a manner that they are kneaded with a kneader and then extruded with an extruder for cement material extrusion.

The present invention is not intended to be limited to any specific kneading methods; however, in the production of extrusion mortar, the kneading is generally carried out in such a manner that an required amount of each ingredient, such as cement, fine aggregate, extruding auxiliary and fiber, is introduced from each hopper into a mixer and fully mixed, after that, a required amount of water is added to and mixed with the mixture, then the mixture is transferred to a kneader, etc., so as to be kneaded.

The kneaded composition is extruded with, for example, a vacuum extruder into various extruded forms such as cement plate, hollow cement plate, cement siding board, column and pipe. These extruded forms are subjected to steam curing or autoclave curing so as to be completed products.

Mortar Thickening Agent

The above-described water-soluble polyurethane according to the present invention is suitably used as a thickening agent for a mortar (a mortar thickening agent).

As a mortar thickening agent, desirably used is the polyurethane in which the molar ratio of the repeating unit (U-1) having the aforementioned general formula (1) is 0.5 or more and 0.99 or less and the molar ratio of the repeating unit (U-2) having the aforementioned general formula (2) is 0.01 or more and 0.5 or less, and whose 2% aqueous solution viscosity at 20° C. is in the range of 10 mPa·s to 300,000 mPa·s.

When polyurethane has a 2% aqueous solution viscosity within this range, it acts on mortar sufficiently as a thickening agent, in addition, its action as a polymer thickening agent is moderate, therefore, the workability of mortar is improved. The polymer having a 2% aqueous solution viscosity at 20° C. is more preferably in the range of 50 to 100,000 mPa·s. The 2% aqueous solution of the polymer is obtained by dissolving 2 g of the polymer in 98 g of distilled water.

For measuring an aqueous solution viscosity, a rotating cylinder viscometer widely use is used. The measurement is carried out using a 2% aqueous solution whose temperature is controlled at 20° C. and at a rotating speed of the cylinder of the viscometer of 6 rpm. However, in cases where the sample has a aqueous solution viscosity exceeding 100,000 mPa·s, the measurement is carried out at a rotating speed of 4 rpm.

For the mortar thickening agents according to the present invention, preferably most of the particles constituting the water-soluble polyurethane powder used have a diameter 1 mm or less. More preferably 95% by weight or more of the particles have a diameter 1 mm or less and 50% by weight or more of the particles have a diameter 600 μm or less. Much more preferably 99% by weight or more of the particles have a diameter 1 mm or less and 50% by weight or more of the particles have a diameter 400 μm or less. When the percentage of the particles having a diameter more than 1 mm is low, the solubility of the water-soluble polyurethane is improved.

The mortar thickening agents may have additives, such as anti-oxidant, stabilizer, plasticizer, dilluent, anti-caking agent and grinding auxiliary, added thereto.

The thickening agents of the present invention are characterized, for example, in that although they cause less retardation of setting than the thickening agents comprising cellulose ethers, they have thickening effects equivalent to the thickening agents comprising cellulose ethers.

The reasons that the thickening agents of the present invention have such excellent characteristics have not been fully clarified yet at present; however, the following discussion may be drawn.

Presumably, the mechanism of cellulose ethers' thickening action in mortar is such that hydrophobic groups such as methyl groups, which are substituents for hydroxyl groups of cellulose units, interact with each other in a hydrophobic manner and polymer chains form an associated molecule via the hydrophobic groups.

On the other hand, the polymers used in the present invention have comb-shaped hydrophobic groups (a kind of aggregate of hydrophobic groups), which originate from comb-shaped hydrophobic diols as a raw material, in their chains and they can form an associated molecule effectively even with a small number of hydrophobic groups. The phenomenon is described in detail in Japanese Patent Laid-Open No. 59-78226 that polymers having aggregates of several hydrophobic groups form a network structure when the aggregates of hydrophobic groups associate with each other, as a result of which the viscosity of the polymer aqueous solution is enhanced.

The mechanism of cellulose ethers' retarding setting of mortar has not been fully clarified yet at present; however, it is presumed that (a) hydroxyl groups of cellulose units bond to calcium in mortar, which retards the hydration reaction of cement and (b) cellulose ethers are adsorbed on cement particles by hydrophobic groups such as methyl group, which retards the hydration reaction of cement.

On the other hand, the polymers used in the present invention have no hydroxyl groups in their repeating units; accordingly, there are unlikely to occur bonding between hydroxyl groups and calcium. In addition, the polymers have only a small number of hydrophobic groups in their chains; therefore, their amount adsorbed on cement particles is small, which causes less retardation of mortar setting than in cases where cellulose ethers are used.

Now the differences between the polymers having hydrophobic aggregates, which are disclosed in Japanese Patent Laid-Open No. 59-78226, (hereinafter referred to as polymers of the literature cited) and the polymers used in the present invention will be described below.

The literature cited discloses that diols having hydrophobic aggregates are obtained by subjecting several molecules of the compounds containing oxirane, such as 1,2-epoxyalkanes, to addition to low-molecular weight diols, such as diethylene glycol, (hereinafter referred to as spacer) using an acid or alkaline catalyst. And alternatively, it discloses that diisocyanates and diols having hydrophobic aggregates are obtained by reacting diols, which are obtained by subjecting 2 molecules of glycidyl ethers to addition to methylamine, with diisocianates.

With these methods, however, hydrophobic aggregates of a fixed number of hydrophobic groups cannot be obtained, and in actuality, obtained was only the mixture of several kinds of hydrophobic aggregates different in the number of hydrophobic groups. This is attributed to the fact that hydroxyl groups produced by the reaction of glycols of the spacer with the compounds containing oxirane further react with the compounds containing oxirane; therefore, various diols are produced which differ in the number of compounds containing oxirane added to the spacer. When bonding diols with diisocyanates, the mixture of several kinds of diisocyanates and diols different in the number of hydrophobic groups is produced.

Thus, it is considered that the polymers of the literature cited are those having a plurality of hydrophobic aggregates different in the number of hydrophobic groups in their molecules.

For the thickening agents using polymers having a plurality of hydrophobic aggregates, which are different in the number of hydrophobic groups, in their molecules, their solubility in mortar is likely to deteriorate and they are likely to cause retardation of mortar setting. Since the number of the hydrophobic groups of each hydrophobic aggregate has distribution, it is unavoidable that the polymers contain hydrophobic aggregates having a large number of hydrophobic groups, and hence, having an unnecessarily strong hydrophobic nature in a certain ratio. Presumably, these hydrophobic aggregates having too strong hydrophobic nature cause the deterioration of solubility of thickening agents and retardation of mortar setting.

On the other hand, the polymers of the present invention are characterized in that they contain hydrophobic aggregates having substantially same number of hydrophobic groups; thus, they can prevent bad effects due to the existence of hydrophobic aggregates having too strong hydrophobic nature.

As described above, the mortar thickening agents of the present invention decrease retardation of setting, which is one of the disadvantages of the currently used thickening agents, while having a thickening effect equivalent to that of the currently used thickening agents. Thus, they are available for a wide range of applications such as tile-bonding mortar, masonry mortar, spraying mortar, repairing mortar, substrate mortar and topping mortar and can contribute greatly to making building construction and public works construction more efficient and more reliable, and reducing the costs thereof.

Mortar Composition

Now the application of the thickening agents comprising the above polymer to mortar thickening agent will be described.

Dry mortar compositions can be obtained by formulating (1) hydraulic inorganic powders such as portland cement, alumina cement and calcium silicate, (2) fine aggregates such as sand, fly ash, silica fume, pearlite, pumice, shattered foamed concrete and shattered foamed plastics and hollow polystyrene particles, and (3) the thickening agents according to the present invention and fully mixing the same. However, the fine aggregates (2) are not always necessary.

In addition to the above ingredients, the other currently used ingredients for the preparation of mortar can be added, according to the need. For example, various types of water reducing agent, reemulsified resin powder, anti-foaming agent and fiber. When these ingredients are powder (solid), these are mixed with the above ingredients (1), (2) and (3), so as to obtain dry mortar.

Suitably, 0.01 to 5% by weight of the thickening agent is added per 100% by weight of all the dry mortar, more preferably 0.1 to 1% by weight.

When the amount of the thickening agent added is in the range of 0.01 to 5% by weight, the effects of thickening agent is developed satisfactorily; in addition, since the amount is a necessary and sufficient amount for obtaining the desired effects of the thickening agent, it is preferable from the economical viewpoint.

The amount of the hydraulic inorganic powder added varies depending on the application of mortar and the amount of the fine aggregate used; however, preferably about 99.99 to 10% by weight is added per 100% by weight of all the dry mortar, preferably 80 to 20% by weight.

The amount of the fine aggregate added varies depending on the application of mortar and the type of the fine aggregate used; however, preferably about 89.99 to 0% by weight is added per 100% by weight of all the dry mortar, preferably 80 to 20% by weight.

When adding water to this dry mortar in such an amount as satisfies the required water-cement ratio (the weight ratio of water to hydraulic inorganic powder) and then fully kneading the mixture, mortar can be obtained.

A suitable water-cement ratio is about 0.2 to 1, more preferably 0.3 to 0.7.

When the water-cement ratio is in the range of 0.2 to 1, the amount of water required for the hydration reaction of cement is ensured, and the strength of mortar after curing becomes satisfactory.

Underwater Concrete Thickening Agent

The above-described water-soluble polyurethane according to the present invention is suitably used as a thickening agent for an underwater concrete (an underwater concrete thickening agent).

As an underwater concrete thickening agent, desirably used is the water-soluble polyurethane according to the present invention in which the molar ratio of the repeating unit (U-1) having the aforementioned general formula (1) is 0.5 or more and 0.99 or less and the molar ratio of the repeating unit (U-2) having the aforementioned general formula (2) is 0.01 or more and 0.5 or less, and preferably the polymer has the weight average molecular weight, which is measured by GPC, in the range of 100,000 to 1,000,000.

In the GPC, chloroform solution was used. And the molecular weight was obtained by calibrating the measurements using standard polystyrene as a standard reference material. When the polyurethane has a weight average molecular weight in the range of 100,000 to 1,000,000, it is suitable to be an underwater concrete thickening agent, because its aqueous solution viscosity is satisfactory and its solution does not show stringiness.

As an underwater concrete thickening agent of the present invention, effectively used is the polyurethane whose 2% aqueous solution viscosity (viscosity of aqueous solution whose polyurethane content is 2% by weight at 20° C. measured with a B type rotating viscometer at 6 rpm) is in the range of about 1,000 to about 500,000 mPa·s, more preferably in the range of 10,000 to 300,000 mPa·s. When polyurethane has a 2% aqueous solution viscosity in the range of about 1,000 to about 500,000 mPa·s, the anti-aggregate-separating properties of concrete is satisfactory, in addition, the tackiness of the same is moderate, therefore, a satisfactory pumpability of concrete is obtained.

When being used as an underwater concrete thickening agent, the above polyurethane may be in the solid flake state and in the distilled aqueous or alcohol solution state; however, more preferably it is in the powder state, in terms of handlability. The powder of particle diameter 16 mesh (1 mm) or less is preferably used. The reason is that the powder of particle diameter 16 mesh (1 mm) or less exhibits a satisfactory solubility.

The above underwater concrete thickening agent may contain an anti-oxidant, a stabilizer, a plasticizer, a diluent, an anti-caking agent, grinding auxiliary, etc. besides the above water-soluble polyurethane as a chief ingredient.

Underwater Concrete Composition

As the compositions for an underwater concrete (an underwater concrete composition) used in the present invention, the compositions equivalent to the known underwater concrete compositions are effectively used, provided that those compositions contain the underwater concrete thickening agents according to the present invention instead of cellulose ethers, such as methyl cellulose and hydroxypropyl methyl cellulose, which have been used as an underwater concrete thickening agent. Specifically, the underwater concrete compositions used in the present invention contain hydraulic powder, such as normal portland cement, special portland cement, portland blastfurnace slag cement, portland fly-ash cement, high alumina cement and plaster, as a chief ingredient, fine aggregates, coarse aggregates and water in addition to the above underwater concrete thickening agent of the present invention.

The compositions may contain, for example, inorganic materials such as fly ash, silica fume, bentonite and clay; reemulsified resin powder; various types of water reducing agents; surfactants; anti-foaming agents, accelerating agents and retarding agents.

The amount of the underwater concrete thickening agent of the present invention added varies depending on the composition of the concrete used; however, the amount is usually about 0.1 to 10% by weight per 100% by weight of hydraulic powder such as cement, more preferably 0.2 to 5% by weight, and much more preferably 0.5 to 5% by weight. When the amount of the underwater concrete thickening agent added is in the range of 0.1 to 10% by weight, the underwater concrete thickening agent works effectively, and it imparts moderate tackiness and it does not allow the workability to deteriorate.

One of the characteristics of the underwater concrete thickening agents of the present invention is that, when being added to cement in the ratio of 10% by weight, they hardly cause retardation of concrete setting. For the currently used thickening agents such as cellulose ethers, however, even when 0.5 to 5% by weight of thickening agents are added per 100% by weight of cement, they are likely to cause retardation of concrete setting, and hence, deterioration of concrete strength.

The method of adding the thickening agents to the concrete may be such that the thickening agents in the powder state are added to and dissolved in concrete while stirring or such that an aqueous solution of the thickening agents is added to concrete or such that the mixture of the underwater concrete thickening agents and cement previously prepared is used as a raw material of concrete.

It goes without saying that the underwater concrete thickening agent of the present invention can be used in combination with the currently used thickening agents such as cellulose ethers, polyacryl polymers, polyethylene oxides and polyvinyl alcohols.

The ratio of water contained in the above composition varies depending on the type and amount of the fine aggregate and coarse aggregate used; however, the suitable weight ratio of water to hydraulic powders, such as cement, (water-cement ratio) is preferably in the range of 0.2 to 1, more preferably in the range of 0.3 to 0.7, and much more preferably 0.3 to 0.5. When the water-cement ratio is in the range of 0.2 to 1, the water content required for the hydration of the cement is moderately ensured, and concrete of satisfactory strength is obtained.

The amount of fine aggregates added may be almost the same as that of the aggregates added to the conventional underwater concrete; typically, the amount of fine aggregates, such as sand, added is about 10 to 500% by weight per 100% by weight of hydraulic powders, such as cement.

The amount of coarse aggregates added may be almost the same as that of the coarse aggregates added to the conventional underwater concret; typically, the amount is about 10 to 500% by weight per 100% by weight of hydraulic powders, such as cement.

Although the present invention is not limited to any specific underwater concrete production methods, the underwater concrete of the present invention can be produced, for example, in such a manner that a predetermined amount of powder of the underwater concrete thickening agents or its aqueous solution is added to and mixed with ready-mixed concrete. Alternatively, the mixture of cement and the powder of the underwater concrete thickening agent previously prepared can be used as a raw material of concrete.

The underwater concrete compositions thus obtained can be placed in the same manner as the currently used concrete. For example, the compositions is supplied underwater by allowing them to freely fall underwater or using a transport pump, or via a bucket, chute, hose or Lamy pipe, then cured underwater.

Ceramics Forming Binder

The above-described water-soluble polyurethanes according to the present invention are suitably used as a ceramics forming binder.

As a ceramics forming binder, preferably used are the polyurethanes in which the molar ratio of the repeating unit (U-1) having the aforementioned general formula (1) is 0.5 or more and 0.99 or less and the molar ratio of the repeating unit (U-2) having the aforementioned general formula (2) is 0.01 or more and 0.5 or less, and the polymers preferably have the weight average molecular weight, as measured by GPC, in the range of 10,000 to 1,000,000, more preferably in the range of 10,000 to 500,000.

In GPC, chloroform solution was used. And the molecular weight was obtained by calibrating the measurements using standard polystyrene as a standard reference material. When the polyurethanes have a weight average molecular weight in the range of 10,000 to 1,000,000, they are suitable to be a binder, because their plasticity and caking are satisfactory.

The ceramics forming binders comprising these polyurethanes are easily dissolved in polar organic solvents such as water and ethanol.

When using these soluble polyurethanes as a ceramics forming binder, other ingredients, which have been used in ceramics forming, may be added to the polyurethanes according to the purpose, so as to obtain ceramics forming compositions. These ingredients include, for example, various types of surfactants, propylene glycol, liquid paraffin, glycerol, ethanolamine, wax emulsion, stearic acid and the salts thereof, alcohols and anti-foaming agents.

The amount of the ceramics forming binder of the present invention varies depending on the type of the ceramic product to be obtained; however, the amount is, for example, preferably about 0.1 to 10% by weight per 100% by weight of ceramics, more preferably 0.5 to 5% by weight.

The present invention is not intended to be limited to any specific ceramics; however, ceramics applicable to the binders of the present invention include not only alumina, but also barium tianate, zirconia, silicon carbide, silicon nitride and other fine ceramics in general.

The ceramics forming binders of the present invention are preferably used as a ceramics extrusion binder. And there are many forming methods to which the binders of the present invention are applicable. Specifically, they are applicable not only to the extrusion process, but also to sheet forming, tape forming and pressing. Since they are thermoplastic resins, they can be used in injection molding. In any cases, they are superior to the currently used binders particularly in their moderate heat release during calcination.

The reasons have not been fully clarified yet that the heat release of the binders of the present invention during combustion is very moderate and the carbon residue content is low; however, presumably, the reasons are that urethane bond is susceptible to thermal decomposition, the elemental structures of the polymers contain a large number of oxygen, therefore, the heat generated due to oxidation is small, and that the molecules do not have a ring structure susceptible to carbonization.

Moisturizer for Hair Cosmetics

The above-described water-soluble polyurethanes according to the present invention are suitably used as a moisturizer for hair cosmetics. The moisturizers according to the present invention, which use these polyurethanes, impart to hair excellent characteristics such as soft feel and neither oily nor dry feel.

As a moisturizer for hair dressing, desirably used are the polyurethanes in which the molar ratio of the repeating unit (U-1) having the aforementioned general formula (1) is 0.5 or more and 0.99 or less and the molar ratio of the repeating unit (U-2) having the aforementioned general formula (2) is 0.01 or more and 0.5 or less, and the polymers preferably have the weight average molecular weight, which is measured by GPC, in the range of 10,000 to 1,000,000, more preferably 10,000 to 500,000.

In GPC, chloroform solution was used. And the molecular weight was obtained by calibrating the measurements using standard polystyrene as a standard reference material. When the polyurethanes have a weight average molecular weight in the range of 10,000 to 1,000,000, they are suitable to be moisturizers for use in hair cosmetics, because they impart satisfactory water retention to hair cosmetics and the hair cosmetics impart to hair moderate feel, neither oily nor dry feel.

The moisturizers for hair cosmetics comprising these polyurethanes are easily dissolved in polar organic solvents such as water and ethanol.

When preparing hair cosmetics using these moisturizers comprising soluble polyurethanes, other ingredients, which have been used in hair cosmetics field, may be added according to the purpose, so as to prepare hair cosmetics compositions. These ingredients include, for example, various types of surfactants, propylene glycol, liquid paraffin, glycerol, silicone oil, ethanol, sequestering agents such as EDTA, perfume, preservatives and purified water.

Industrial Field of the Invention

As describe above, according to the present invention, polyurethanes having improved characteristics such as viscosity characteristics, solubility and moisture retention can be obtained.

As a result, extruding auxiliaries are available which have high shape retention as well as improved solubility, and what is more, are inexpensive. Further, with these extruding auxiliary, the shape retention of mortar using asbestos-substitute fibers can be improved. And moreover, extruded cement plates having improved strength can be obtained.

Further, mortar thickening agents can be obtained which have thickening effects equivalent to those of the currently used thickening agents, though they cause less retardation of setting, and which can impart to mortar thixtropic properties as well as water retention necessary and sufficient for placing of mortar. Thus, in building construction and public works construction, these mortar thickening agents can contribute largely to making their processes more efficient, improving their reliability and reducing their costs.

Still further, according to the present invention, underwater concrete thickening agents are available which can impart high underwater anti-separating properties as well as improved strength to underwater concrete, and what is more, are inexpensive.

Further, according to the present invention, cersmics forming binders having a high productivity are available.

Still further, according to the present invention, moisturizers for use in hair cosmetics are available which have high moisture retention and can impart moist feel to hair.

EXAMPLES

The present invention will be described with reference to the following examples; however, it is to be understood that these examples are not intended to limit the present invention.

(Examples of Comb-shaped Hydrophobic Diol Syntheses)

Example A-1

A 500 ml round flask was equipped with a magnetic stirrer, a thermometer and a dropping funnel, 64.6 g of 2-ethylhexylamine (available from Kanto Chemical Co., Inc.) was put into the flask, and the inside of the flask was displaced with nitrogen. The flask was heated to 60° C. in an oil bath, 188.0 g of 2-ethylhexylglycidyl ether (available from Nagase Chemicals Ltd., Denacol EX-121, epoxy number 188) was dropped from the dropping funnel over 40 minutes while stirring. After completion of the dropping, the temperature of the oil bath was raised to 80° C. and the flask was heated for 10 hours. Then the temperature of the oil bath was further raised to 120° C., a small amount of unreacted substance was distilled off under reduced pressure with a vacuum pump at a vacuum degree of 3 mmHg. Comb-shaped hydrophobic diol (A-1) (average molecular weight obtained from OH value was 490) in which 2-ethylhexylglycidyl ether was subjected to addition to 2-ethylhexylamine in the ratio of 2:1 mole was obtained in a yield of 98%.

Example A-2

Comb-shaped hydrophobic diol A-2 was synthesized by subjecting n-butylglycidyl ether (available from TOKYO KASEI KOGYO CO., LTD.) to addition to n-butylamine (available from TOKYO KASEI KOGYO CO., LTD.) in the ratio of 2:1 mole.

Example A-3

Comb-shaped hydrophobic diol A-3 was synthesized by subjecting 2-ethylhexylglycidyl ether to addition to n-butylamine in the ratio of 2:1 mole.

Example A-4

Comb-shaped hydrophobic diol A-4 was synthesized by subjecting 2-ethylhexylglycidyl ether to addition to dodecylamine (available from Kanto Chemical Co., Inc.) in the ratio of 2:1 mole.

Example A-3

Comb-shaped hydrophobic diol A-3 was synthesized by subjecting dodecylglycidyl ether (obtained by subjecting dodecyl/tetradecylglycidyl ether manufactured by Ardrich to distillation purification) to addition to n-octylamine (available from TOKYO KASEI KOGYO CO., LTD.) in the ratio of 2:1 mole.

Example A-6

Comb-shaped hydrophobic diol A-6 was synthesized by subjecting n-octylglycidyl ether (P & B) to addition to n-octadecylamine (available from Kanto Chemical Co., Inc.) in the ratio of 2:1 mole.

Example A-7

Comb-shaped hydrophobic diol A-7 was synthesized by subjecting octadecylglycidyl ether (available from NOF Corp., Epiol SK) to addition to n-butylamine in the ratio of 2:1 mole.

These results are shown in Table A-1.

TABLE A-1

Table A-1 Examples of Comb-shaped Hydrophobic Diol Syntheses (1)
Structural Formula of Compounds:
$R^2$—$OCH_2CH(OH)CH_2N(R^1)CH_2CH(OH)CH_2O$—$R^3$

| Run Number | $R^1$ | $R^2$, $R^3$ | Molecular Weight obtained from OH value |
|---|---|---|---|
| Example A-1 | —$CH_2CH(CH_2)_3CH_3$ <br> └—$CH_2CH_3$ | —$CH_2CH(CH_2)_3CH_3$ <br> └—$CH_2CH_3$ | 490 |
| Example A-2 | —$(CH_2)_3CH_3$ | —$(CH_2)_3CH_3$ | 332 |
| Example A-3 | —$(CH_2)_3CH_3$ | —$CH_2CH(CH_2)_3CH_3$ <br> └—$CH_2CH_3$ | 438 |
| Example A-4 | —$(CH_2)_{11}CH_3$ | —$CH_2CH(CH_2)_3CH_3$ <br> └—$CH_2CH_3$ | 554 |
| Example A-5 | —$(CH_2)_7CH_3$ | —$(CH_2)_{11}CH_3$ | 585 |
| Example A-6 | —$(CH_2)_{17}CH_3$ | —$(CH_2)_7CH_3$ | 630 |
| Example A-7 | —$(CH_2)_3CH_3$ | —$(CH_2)_{17}CH_3$ | 720 |

In order to compare the dispersion degree of hydrophobic diols and the characteristics of polyurethanes, an example of the syntheses of the currently used diol whose dispersion degree is high will be shown as comparative example A-1.

Comparative Example A-1

A 500 ml round flask was equipped with a magnetic stirrer, a thermometer and a dropping funnel, 26.5 g of diethylene glycol (available from TOKYO KASEI KOGYO CO., LTD.) was put into the flask, and the inside of the flask was displaced with nitrogen. The flask was heated to 50° C. in an oil bath, 0.35 ml of trifluoroboron ether complex was added as a catalyst, 188 g of 2-ethylhexylglycidyl ether (available from Nagase Chemicals Ltd., epoxy number 188) was dropped slowly from the dropping funnel over 2 hours, while stirring and taking care that the temperature of the product is not allowed to exceed 70° C. After completion of the dropping, the temperature of the oil bath was raised to 80° C. and the flask was heated for 2 hours. Then the temperature of the oil bath was further raised to 100° C., the catalyst was distilled off under reduced pressure with a vacuum pump at a vacuum degree of 2 mmHg. Hydrophobic diol (average molecular weight obtained from OH value was 834) in which 2-ethylhexylglycidyl ether was subjected to addition to diethylene glycol in the ratio of 4:1 mole was obtained.

(GPC Analysis of Hydrophobic Diols)

Hydrophobic diols in chloroform was allowed to separate by the recycle GPC and detected with a differentia refractometer. The apparatus used in the analysis was LC-908 manufactured by Nippon Chemical Analysis Industry Co., Ltd. and columns, which were 2H and 1H from the same company, were connected in series.

FIG. A-1 shows the measured results of the diols of the example A-1 and comparative example A-1 obtained by the analyses under the same conditions, as one typical example. The retention time is plotted in abscissa and the signal strength is plotted in ordinate.

The diol of the comparative example A-1 was a mixture of the components having different number of glycidyl ether added while the comb-shaped hydrophobic diol of the example A-1 mostly comprising a single component.
(Examples of Water-Soluble Polyurethane Syntheses)

Examples of syntheses of water-soluble polyurethane using the hydrophobic diol of the example A-1 will be described below; however, it should be understood that these examples are not intended to limit the present invention.

Example A-8

100 g of commercially available PEG#6000 (available from JUNSEI CHEMICAL CO., LTD., number average molecular weight 8,700) was put into a 500 ml separable flask manufactured by SUS and was allowed to melt under nitrogen seal at 150° C. This molten PEG was subjected to drying under reduced pressure (3 mmHg) for 3 hours while stirring. The residual water content was 200 ppm. The temperature of the flask was reduced to 80° C., and 0.85 g of the comb-shaped hydrophobic diol A-1 obtained in the example A-1 and 2.30 g of hexamethylenediisocyanate (available from TOKYO KASEI KOGYO CO., LTD.) were put into the flask while stirring. When adding 0.01 g of DBTDL as a catalyst, the content of the flask was rapidly thickened after about 10 minutes. The reaction was allowed to progress for another two hours while stopping stirring. After completion of the reaction, the product was taken out from the flask, cut into small pieces and allowed to stand to be cooled. The cooled product was further cooled with liquid nitrogen and pulverized into particles of diameter 1 mm (16 mesh) or smaller with an electric mill. The 2.5% aqueous solution viscosity of the product was 350,000 mPa·s and the weight average molecular weight of the same was 520,000.

Examples A-9 to A-14

Water-soluble polyurethanes were synthesized in the same manner as in the example A-8, except that the amount of each of the comb-shaped hydrophobic diol A-1 and HDI put into the flask was different. Each amount was set so that the number of moles of HDI would become 1.03 times as large as the total number of moles of PEG and the comb-shaped hydrophobic diol (NCO/OH=1.03).

The results are shown in Table A-2.

Comparative Examples A-2 to A-6

Polyurethane was synthesized using the same type of diol whose dispersion degree is high as used in the comparative example A-1. NCO/OH was 1.03. The results are shown in Table A-2 together with those of the examples A-8 to A-14.

TABLE A-2

Examples of Water-soluble Polyurethane Syntheses (1)

| Run Number | Molecular Weight of PEG | Type of Hydrophobic Diol | Total Number of Carbon Atoms of Hydrophobic Groups | Hydrophobic Diol/PEG (%) | Coefficient of Repeating Unit X | 2.5% Aqueous Solution Viscosity (mPa's) | Weight Average Molecular Weight ($\times 10^4$) |
|---|---|---|---|---|---|---|---|
| Example A-8 | 8,700 | Example A-1 | 24 | 0.85 | 0.13 | 350,000 | 52 |
| Example A-9 | 8,700 | Example A-1 | 24 | 1.1 | 0.16 | 440,000 | 50 |
| Example A-10 | 8,700 | Example A-1 | 24 | 1.0 | 0.15 | 500,000 | 55 |
| Example A-11 | 8,700 | Example A-1 | 24 | 0.9 | 0.14 | 440,000 | 53 |
| Example A-12 | 8,700 | Example A-1 | 24 | 0.8 | 0.12 | 250,000 | 50 |
| Example A-13 | 8,700 | Example A-1 | 24 | 0.75 | 0.12 | 150,000 | 53 |
| Example A-14 | 8,700 | Example A-1 | 24 | 0.6 | 0.10 | 3,000 | 60 |
| Comparative example A-2 | 8,700 | Comparative example A-1 | 32 | 0.96 | 0.09 | 4,600 | 50 |
| Comparative example A-3 | 8,700 | Comparative example A-1 | 32 | 0.84 | 0.08 | 130,000 | 52 |
| Comparative example A-4 | 8,700 | Comparative example A-1 | 32 | 0.8 | 0.08 | 290,000 | 53 |
| Comparative example A-5 | 8,700 | Comparative example A-1 | 32 | 0.74 | 0.07 | 220,000 | 50 |
| Comparative example A-6 | 8,700 | Comparative example A-1 | 32 | 0.48 | 0.05 | 8,200 | 55 |

Examples A-15 to A-24

Water-soluble polyurethanes were synthesized in the same manner as in the example A-8, except that the type of hydrophobic diol and the amount of each of the comb-shaped hydrophobic diol put into the flask were different. However, for the PEG used in the examples A-23 and A-24, its molecular weight was a little different from the others' since its synthesis lot was different from the others'.

Examples A-25 to A-26

Commercially available PEG#4000 (number average molecular weight 3,000) was used as PEG.

Examples A-27 to A-28

Commercially available PEG#20000 (number average molecular weight 20,000) was used as PEG.

The results are shown in Table A-3.

TABLE A-3

Examples of Water-soluble Polyurethane Syntheses (2)

| Run Number | Molecular Weight of PEG | Type of Hydrophobic Diol | Total Number of Carbon Atoms of Hydrophobic Groups | Hydrophobic Diol/PEG (%) | Coefficient of Repeating Unit X | 2.5% Aqueous Solution Viscosity (mPa's) | Weight Average Molecular Weight (×10$^4$) |
|---|---|---|---|---|---|---|---|
| Example A-15 | 8,700 | Example A-2 | 12 | 2.5 | 0.40 | 100,000 | 38 |
| Example A-16 | 8,700 | Example A-2 | 12 | 1.5 | 0.28 | 1,000 | 35 |
| Example A-17 | 8,700 | Example A-3 | 20 | 1.3 | 0.21 | 490,000 | 42 |
| Example A-18 | 8,700 | Example A-3 | 20 | 0.6 | 0.11 | 1,300 | 45 |
| Example A-19 | 8,700 | Example A-4 | 28 | 0.6 | 0.09 | 370,000 | 47 |
| Example A-20 | 8,700 | Example A-4 | 28 | 0.45 | 0.07 | 310,000 | 49 |
| Example A-21 | 8,700 | Example A-5 | 32 | 1.0 | 0.13 | 980,000 | 46 |
| Example A-22 | 8,700 | Example A-5 | 32 | 0.3 | 0.04 | 110,000 | 48 |
| Example A-23 | 8,500 | Example A-6 | 34 | 0.3 | 0.04 | 300,000 | 55 |
| Example A-24 | 8,500 | Example A-7 | 40 | 0.2 | 0.03 | 200,000 | 39 |
| Example A-25 | 3,000 | Example A-1 | 24 | 1.0 | 0.06 | 5,000 | 10 |
| Example A-26 | 3,000 | Example A-7 | 40 | 0.2 | 0.01 | 2,000 | 13 |
| Example A-27 | 20,000 | Example A-1 | 24 | 0.6 | 0.21 | 80,000 | 100 |
| Example A-28 | 20,000 | Example A-2 | 12 | 1.6 | 0.50 | 300,000 | 90 |

In Table A-2 and Table A-3, "Molecular Weight of PEG" means the number average molecular weight of PEG obtained from OH value (OHV). "Total Number of Carbon Atoms of Hydrophobic Groups" means the total number of carbon atoms of the hydrophobic groups $R^1$, $R^2$ and $R^3$ of the above-described hydrophobic diol.

"Hydrophobic Diol/PEG" means the weight ratio of the raw materials of the hydrophobic diol to PEG expressed as the percentage. "Coefficient of Repeating Unit x" means the coefficient x of the repeating unit having the aforementioned general formula 10. "2.5% Aqueous Solution Viscosity" means the water-soluble polyurethane aqueous solution viscosity (the unit is mPa·s) whose water-soluble polyurethane concentration is 2.5% by weight measured with a B type rotating viscometer at 6 rpm at 25° C. "Weight Average Molecular Weight" means the molecular weight measured by the GPC using monodisperse polystyrene as a standard reference material. As a solvent, chloroform was used. When x is in the range of 0.01 to 0.5 and the weight average molecular weight is in the range of 100,000 to 1,000,000, water-soluble polyurethanes whose 2.5% aqueous solution viscosity is 1,000 to 1,000,000 mPa·s are obtained.

(Improvement in Solubility)

In FIG. A-2, the variation of aqueous solution viscosity of hydrophobic diols is shown when weight ratio of hydrophobic diols to PEG (hydrophobic diol/PEG). A comparison is made between the cases where substantially monodisperse comb-shaped hydrophobic diol is used (the examples A-8 to A-14) and the case where polydisperse comb-shaped hydrophobic diol is used (the comparative examples A-2 to A-6). The polymers containing monodisperse and polydisperse comb-shaped hydrophobic diols are almost the same in weight average molecular weight, however, they are greatly different in the variation of aqueous solution viscosity with "hydrophobic diol/PEG." In cases where polydisperse hydrophobic diol is used, when the "hydrophobic diol/PEG" value exceeds a certain value (threshold value), the solubility of polyurethane is decreased, thereby the aqueous solution viscosity is rapidly decreased. On the other hand, in cases where monodisperse hydrophobic diol is used, it cannot be noticed that the "hydrophobic diol/PEG" values have a threshold at which the aqueous solution viscosity is rapidly changed. It is obvious that, in cases where substantially monodisperse hydrophobic diol is used, a higher aqueous solution viscosity can be realized without deteriorating its solubility by controlling the amount of the hydrophobic diol. In addition, because there exists no threshold value, even if the amount of the hydrophobic diol varies a little, the solubility does not decrease; therefore, a major advantage is offered in terms of the production of water-soluble polyurethanes.

Application to Extruding Auxiliary (Extrusion Test)

Examples A-29 to A-44, Comparative Examples A-7 to A-10

Extrusion tests were conducted on plate-shaped extruded forms (cement plates) using mortar comprising cement, sand, asbestos-substitute fiber, extruding auxiliary and water. 100 parts by weight of normal portland cement, 100 parts by weight of standard sand, 1.5 parts by weight of vinylon fiber (available from Unitika, Vinylon Type AB Semi-hard) and a predetermined amount of extruding auxiliary were mixed with a high-speed mixer (Miyazaki Iron Works, Ltd., MHS-100) for 3 minutes. Then, water was added to this composition so that the composition had a predetermined water-cement ratio, the mixture was mixed for another 3 minutes, so as to obtain an extruding composition of cement material. The mortar thus obtained was kneaded with a screw-type kneader (available from Miyazaki Iron Works, Ltd., MP-30-1). The kneaded material was extruded with a screw-type vacuum extruding machine (available from Miyazaki Iron Works, Ltd., FM-30-1) at a fixed extrusion speed into plate-shaped forms 10 mm thick and 20 mm wide. The extruded forms were subjected to underwater curing for 28 days, after that, their flexural strength was measured.

Table A-4 shows the type of extruding auxiliary used in each example and comparative example, the amount of the extruding auxiliary added (% by weight to the cement), the ratio of water-cement (W/C) contained in the mortar, the occurrence of water separation during the extrusion, the surface topology, the shape retention of the extruded forms and the flexural strength after curing.

Whether water separation occurred or not was judged by observing the water flow from the die portion during the extrusion. When no water separation was observed, the condition was judged to be good (A). When a little water separation was observed, but extrusion could be carried out, the condition was judged to be fair (B). And when water separation was clearly observed and extrusion could not be carried out, the condition was judges to be failure (C).

For the judgment of the surface topology, when the surface of the extruded form was smooth immediately after extrusion, the condition was judged to be good (A). When a little irregularity was observed, the condition was judged to be fair (B). And when irregularity was clearly observed, the condition was judges to be failure (C). The shape retention of the extruded form was judged in such a manner that, first the extruded form immediately after extrusion was cut into pieces 20 cm long, each of the pieces were placed across the two blocks spaced at intervals of 10 cm and left stand at temperature of 25° C. and humidity of 100% for 24 hours, and finally the distance of the sag in the middle portion of the extruded form was measured. When the sag was less than 15 mm, the condition was judged to be good (A). When the sag was 15 mm or longer and less than 20 mm, the condition was judged to be fair (B). And when the sag was 20 mm or longer, the condition was judges to be failure (C). The flexural strength was measured in accordance with JIS R-5201. For comparison, other examples are shown: three examples in which the currently used commercially available extruding auxiliary, hydroxypropylmethyl cellulose (90SH-30000 manufactured by Shin-Etsu Chemical Co., Ltd.), was used and the other one in which no extruding auxiliary was used.

Comparing the examples A-29 to A-44 and the comparative examples A-7 to A-9, it is obvious that the extruding auxiliaries according to the present invention have water retention at least equivalent to and shape retention superior to the commercially available extruding auxiliaries (water-soluble cellulose ethers). The shape retention may reflect the excellent thixotropic properties of the mortar. The reason is not fully clear; however, it is considered that the excellent thixotropic properties of the mortar (extrusion composition of the cement material) according to the present invention reflect not only the high viscosity of the polyurethane aqueous solution, but also the effects of the moderate interactions between the comb-shaped hydrophobic group of the polyurethane and the cement particles.

For the mortar using the commercially available extruding auxiliaries, its shape retention is not satisfactory. Needless to say, if the amount of the asbestos-substitute fiber added is increased, the shape retention will be improved; however, it is not preferable to increase such an amount because doing so will result in a remarkable rise in costs of producing extruded forms. The extruded cement plate according to the present invention has an improved flexural strength compared with those using commercially available extruding auxiliaries (water-soluble cellulose ethers). The reasons are, for example, that, when using the extruding auxiliaries of the present invention, vacuum defoaming of mortar can be carried out effectively compared with the mortar using commercially available extruding auxiliary and the polymers of the present invention do not cause retardation of

TABLE A-4

Results of Extrusion Test (1)

| Run Number | Type of Extruding Auxiliary | Amount of Extruding Auxiliary Added (% by weight of cement) | Water-Cement Ratio | Occurrence of Water Separation | Surface Topology | Shape Retention | Flexural Strength (kg/cm$^2$) |
|---|---|---|---|---|---|---|---|
| Example A-29 | Example A-8 | 1.0 | 0.35 | A | A | A | 145 |
| Example A-30 | Example A-10 | 0.8 | 0.40 | A | A | A | 140 |
| Example A-31 | Example A-15 | 1.0 | 0.30 | A | A | A | 150 |
| Example A-32 | Example A-16 | 1.5 | 0.30 | A | A | A | 160 |
| Example A-33 | Example A-17 | 0.5 | 0.30 | A | A | A | 150 |
| Example A-34 | Example A-18 | 1.5 | 0.35 | A | A | A | 145 |
| Example A-35 | Example A-19 | 1.0 | 0.35 | B | A | A | 145 |
| Example A-36 | Example A-20 | 1.0 | 0.35 | A | A | A | 145 |
| Example A-37 | Example A-21 | 1.0 | 0.40 | B | B | A | 140 |
| Example A-38 | Example A-22 | 1.0 | 0.35 | A | A | A | 145 |
| Example A-39 | Example A-23 | 1.0 | 0.35 | B | A | A | 145 |
| Example A-40 | Example A-24 | 1.0 | 0.35 | B | A | A | 145 |
| Example A-41 | Example A-25 | 1.5 | 0.35 | A | A | B | 145 |
| Example A-42 | Example A-26 | 2.0 | 0.40 | A | A | B | 140 |
| Example A-43 | Example A-27 | 1.0 | 0.35 | A | B | A | 145 |
| Example A-44 | Example A-28 | 1.0 | 0.40 | A | B | A | 140 |
| Comparative example A-7 | Commercially Available Extruding Auxiliary | 1.5 | 0.35 | — (*1) | — | — | — |
| Comparative example A-8 | Commercially Available Extruding Auxiliary | 1.0 | 0.30 | A | A | C | 130 |
| Comparative example A-9 | Commercially Available Extruding Auxiliary | 1.5 | 0.30 | B | A | C | 130 |
| Comparative example A-10 | No Extruding Auxiliary Added | — | 0.35 | C (*2) | — | — | — |

*1: The extrusion test was stopped because the mortar was strongly blown in a vacuum defoaming room of the extruding machine.
*2: The extrusion test was stopped because water was separated from the mortar during extruding.

hardening, which is one of disadvantages of water-soluble cellulose ethers, so often.

Application to Mortar Thickening Agent

Example B-1

A 500 ml round flask was equipped with a magnetic stirrer, a thermometer and a dropping funnel, 64.6 g of 2-ethylhexylamine (available from Kanto Chemical Co., Inc.) was put into the flask, and the inside of the flask was displaced with nitrogen. The flask was heated to 60° C. in an oil bath, 220.0 g of 2-ethylhexylglycidyl ether (available from Asahi Denka Kogyo K.K., AdekaGlycylol ED 518, epoxy number 220) was dropped from the dropping funnel over 40 minutes while stirring. After completion of the dropping, the temperature of the oil bath was raised to 80° C. and the flask was heated for 10 hours. Then the temperature of the oil bath was further raised to 120° C., a small amount of unreacted substance was distilled off under reduced pressure with a vacuum pump at a vacuum degree of 3 mmHg. Comb-shaped hydrophobic diol B-1 (average molecular weight obtained from OH value was 532) in which 2-ethylhexylglycidyl ether was subjected to addition to 2-ethylhexylamine in the ratio of 2:1 mole was obtained in a yield of 90%.

(Examples of Polymer Syntheses)

Examples of polymer syntheses using the hydrophobic diol B-1 of the example B-1 will be described below; however, it should be understood that these examples are not intended to limit the present invention.

Example B-2

200 g of commercially available PEG#6000 (available from Sanyo Chemical Industries, Ltd., number average molecular weight 8,630) was put into a 1000 ml separable flask manufactured by SUS and was allowed to melt under nitrogen seal at 150° C. This molten PEG was subjected to drying under reduced pressure (3 mmHg) for 3 hours while stirring. The residual water content was 200 ppm. The temperature of the flask was reduced to 70° C., and the inside of the flask was packed with 1 atom of nitrogen. 300 ppm of BHT (di-tert-butylhydroxytoluene) was added as an anti-oxidant. 1.70 g of the comb-shaped hydrophobic diol B-1 obtained in the example B-1 and 4.35 g of hexamethylenediisocyanate (available from TOKYO KASEI KOGYO CO., LTD.) (NCO/OH=0.98 mol/mol) were put into the flask while stirring. When adding 0.05 g of DBTDL as a catalyst, the content of the flask was rapidly thickened after about 10 minutes. The reaction was allowed to progress for another two hours at 70° C. while stopping stirring. The temperature of the flask was raised to 120° C. and kept the same for 30 minutes, then the product was taken out from the flask. The melting point of the product was about 60° C.

The product taken out from the flask was cut into small pieces and allowed to stand to be cooled. The cooled product was further cooled with liquid nitrogen and pulverized with a small impact electric mill. The pulverized product was sieved, so as to obtain powder of diameter 600 µm or smaller as a mortar thickening agent. The average particle diameter of the powder was 400 µm.

2 g of this polymer was dissolved in 98 g of distilled water so as to obtain 2% aqueous solution. This aqueous solution was put into a beaker, the beaker was immersed in a constant temperature bath kept at 20° C., and the viscosity of the aqueous solution was measured with a rotating cylinder viscometer (BL type viscometer manufactured by TOKIMEC) at the revolution number of rotor of 6 rpm. The viscosity thus obtained was 15,000 mPa·s (15,000 centipoise).

Example B-3

200 g of commercially available PEG#6000 (available from Sanyo Chemical Industries, Ltd., number average molecular weight 8,630) was put into a 1000 ml separable flask manufactured by SUS and was allowed to melt under nitrogen seal at 150° C. This molten PEG was subjected to drying under reduced pressure (3 mmHg) for 3 hours while stirring. The residual water content was 200 ppm. The temperature of the flask was reduced to 70° C., and the inside of the flask was packed with 1 atom of nitrogen. 300 ppm of BHT (di-tert-butylhydroxytoluene) was added as an anti-oxidant. 1.90 g of the comb-shaped hydrophobic diol B-1 obtained in the example B-1 and 4.41 g of hexamethylenediisocyanate (available from TOKYO KASEI KOGYO CO., LTD.) (NCO/OH=0.98 mol/mol) were put into the flask while stirring. When adding 0.05 g of DBTDL as a catalyst, the content of the flask was rapidly thickened after about 10 minutes. The reaction was allowed to progress for another two hours at 70° C. while stopping stirring. The temperature of the flask was raised to 120° C. and kept the same for 30 minutes, then the product was taken out from the flask. The melting point of the product was about 60° C.

The product taken out from the flask was cut into small pieces and allowed to stand to be cooled. The cooled product was further cooled with liquid nitrogen and pulverized with a small impact electric mill. The pulverized product was sieved, so as to obtain powder of diameter 600 µm or smaller as a mortar thickening agent. The average particle diameter of the powder was 400 µm.

2 g of this polymer was dissolved in 98 g of distilled water so as to obtain 2% aqueous solution. This aqueous solution was put into a beaker, the beaker was immersed in a constant temperature bath kept at 20° C., and the viscosity of the aqueous solution was measured with a rotating cylinder viscometer (BL type viscometer manufactured by TOKIMEC) at the revolution number of rotor of 6 rpm. The viscosity thus obtained was 48,000 mPa·s (48,000 centipoise).

(Examples of Mortar Production Using Mortar Thickening Agent)

Examples of mortar production using the mortar thickening agents of the examples B-2 and B-3 will be described below; however, it should be understood that these examples are not intended to limit the present invention.

Example B-4

400 g of portland cement, 400 g of standard sand and 1.6 g of the thickening agent of the example B-2 were put into a mortar mixer and mixed while stirring for 10 minutes, so as to obtain dry mortar. 180 g of water was added to this dry mortar (water-cement ratio 0.45), stirred for 5 minutes, so as to obtain thickened mortar.

The viscosity of this mortar at room temperature (21 to 22° C.) was measured with a rotating cylinder viscometer (B8M Type manufactured by TOKIMEC) at rotary speeds of the rotor of 0.6 to 60 rpm.

Example B-5

Mortar was produced in the same manner as in the example B-4, except that the thickening agent of the example B-3 was used.

Comparative Example B-1

Mortar was produced in the same manner as in the example B-4, except that no thickening agent was used.

Comparative Example B-2

Mortar was produced in the same manner as in the example B-4, except that instead of the thickening agent of the example B-4, the same amount of methyl cellulose was used. The viscosity of the mortar was measured in the same manner as in the example B-4. As methyl cellulose, used was hi Metholose 90SH-15000 (2% aqueous solution viscosity is 15,000 mPa·s) manufactured by Shin-Etsu Chemical Co., Ltd., which was almost the same 2% aqueous solution viscosity as that of the thickening agent produced in the example B-2. The composition of each mortar is shown in Table B-1.

TABLE B-1

Composition of Mortar

| Type of Mortar | Cement (g) | Sand (g) | Thickening Agent Type | Amount (g) | Water (g) |
|---|---|---|---|---|---|
| Example B-4 | 400 | 400 | Example B-2 | 1.6 | 180 |
| Example B-5 | 400 | 400 | Example B-3 | 1.6 | 180 |
| Comparative example B-1 | 400 | 400 | None | 0 | 180 |
| Comparative example B-2 | 400 | 400 | Metholose | 1.6 | 180 |

The relationship between viscosity of the mortar and rotary speed of the rotor used in the measurement thereof is shown in FIG. B-1. In FIG. B-1, 1 is a curve of viscosity of the mortar in Example B-4, 2 is a curve of viscosity of the mortar in Example B-5, 3 is a curve of viscosity of the mortar in Comparative Example B-1 and 4 is a curve of the mortar in Comparative Example B-2. It is observed that in all the examples the viscosity is decreased as the rotary speed becomes high. This phenomenon reflects the thixotropic properties of the mortar. It is obvious that the use of a thickening agent increased the viscosity of the mortar. The increase in viscosity at lower rotary speeds (lower shear force) serves to suppress the flow of mortar after placing and prevent sags from occurring. And the decrease in viscosity at higher rotary speeds (higher shear force) is a characteristic necessary for mortar to separate from a trowel satisfactorily.

The mortar in the example B-4 and the comparative example B-2 had almost the same viscosity. It is considered to be attributed to the fact that the mortar thickening agent has almost the same 2% aqueous solution viscosity. The mortar in the example B-5 had a higher viscosity than the mortar using the above two thickening agents. It is considered to be attributed to the fact that the 2% aqueous solution viscosity of the thickening agent is higher than those of the above two thickening agents.

As mortar thickening agents, various cellulose ethers differing in aqueous solution viscosity are used depending on their applications. However, thickening agents having a 2% aqueous solution viscosity in the range of 100 to 300,000 mPa·s can be obtained according to the present invention; accordingly, in almost all the applications, the currently used thickening agents such as methyl cellulose can be replaced with the thickening agents of the present invention.

(Setting Retardation of Mortar)

As a problem which arises when using cellulose ethers as a thickening agents, it is widely known that the setting of mortar is retarded and the development of the initial strength of the mortar is also retarded.

The initial setting time of each mortar produced in the example B-4, comparative examples B-1 and B-2 was measured with a Vicat needle apparatus manufactured in accordance with JIS R5201 by Maruto Testing Machine Company.

The mortar was packed into a container 40 mm deep, a predetermined initial needle was dropped on the mortar in a predetermined manner, the position at which the needle stopped was read using the graduations on the needle. The measurement was made at intervals of 30 minutes since the instance of adding water to the mortar. When the distance of the position at which the needle stopped from the bottom of the container was 1 mm or more, setting was considered to start, and the elapsed time of setting since the instance of adding water to the mortar was defined as initial setting time. The difference from the initial setting time of the comparative example B-1 was defined as setting retardation time. The presence of bleeding on the mortar surface was checked by visual observation in 3 hours after the addition of water to the mortar. The results are shown in Table B-2.

TABLE B-2

Initial Setting Time of Mortar and Presence of Bleeding

| Type of Mortar | Initial Setting Time (hour) | Setting Retardation Time (hour) | Bleeding |
|---|---|---|---|
| Example B-4 | 6.0 | 2.5 | absent |
| Comparative example B-1 | 3.5 | 0 | present |
| Comparative example B-2 | 8.0 | 4.5 | absent |

As can be seen from Table B-2, for the mortar of the example B-4, its retardation of setting is shorter than that of the mortar of the comparative example B-2 and the phenomenon of bleeding, which is observed in the mortar of the comparative example B-1, is satisfactorily suppressed.

It is obvious that the thickening agents of the present invention have the thickening effect equivalent to that of the commercially available thickening agents and impart to mortar thixotropic properties and water retention necessary for placing thereof, though their retardation of setting is shorter than the commercially available thickening agents.
Application to Underwater Concrete Thickening Agent
(Comb-Shaped Hydrophobic Diols)

The same hydrophobic diols as prepared in the examples A-1 to A-7 were used.
(Examples of Water-Soluble Polyurethane Syntheses)

Examples of synthesis of water-soluble polyurethanes using the hydrophobic diol of the example A-1 will be described below; however, it should be understood that these examples are not intended to limit the present invention.

Example C-1

100 g of commercially available PEG#6000 (available from JUNSEI CHEMICAL CO., LTD., number average molecular weight 8, 700) was put into a 500 ml separable flask manufactured by SUS and was allowed to melt under nitrogen seal at 150° C. This molten PEG was subjected to drying under reduced pressure (3 mmHg) for 3 hours while stirring. The residual water content was 200 ppm. The temperature of the flask was reduced to 80° C., and 1.00 g of the comb-shaped hydrophobic diol A-1 obtained in the example A-1 and 2.35 g of hexamethylenediisocyanate (TOKYO KASEI KOGYO CO., LTD., HDI) were put into the flask while stirring. When adding 0.01 g of DBTDL as a catalyst, the content of the flask was rapidly thickened after about 10 minutes. The reaction was allowed to progress for another two hours while stopping stirring.

After completion of the reaction, the product was taken out from the flask, cut into small pieces and allowed to stand to be cooled. The cooled product was further cooled with liquid nitrogen and pulverized into particles of diameter 1 mm (16 mesh) or smaller with an electric mill.

The 2% aqueous solution viscosity of the product thus obtained was 200,000 mPa·s and the weight average molecular weight measured by GPC was 550,000.

Examples C-2 to C-5

Water-soluble polyurethanes C-2 to C-5 were synthesized in the same manner as in the example C-1, except that the amount of each of the comb-shaped hydrophobic diol A-1 and HDI put into the flask was different.

Each amount was set so that the number of moles of HDI would become 1.03 times as large as the total number of moles of PEG and the comb-shaped hydrophobic diol (NCO/OH=1.03). The results are shown in Table C-1.

In Table C-1 and Table C-2, "Molecular Weight of PEG" means the number average molecular weight of PEG obtained from OH value (OHV).

"Total Number of Carbon Atoms of Hydrophobic Groups" means the total number of carbon atoms of the hydrophobic groups $R^1$, $R^2$ and $R^3$ of the above-described hydrophobic diol.

"Hydrophobic Diol/PEG" means the weight ratio of the raw materials of the hydrophobic diol to PEG expressed as the percentage. "Coefficient of Repeating Unit x" means the coefficient x of the repeating unit having the aforementioned general formula 10.

"2% Aqueous Solution Viscosity" means the water-soluble polyurethane aqueous solution viscosity (the unit is

TABLE C-1

Example of Water-soluble Polyurethane Syntheses (1)

| Run Number | Molecular Weight of PEG | Type of Hydrophobic Diols | Total Number of Carbon Atoms of Hydrophobic Groups | Hydrophobic Diol/PEG (%) | Coefficient of Repeating Unit X | 2% Aqueous Solution Viscosity (mPa · s) | Weight Average Molecular Weight ($\times 10^4$) |
|---|---|---|---|---|---|---|---|
| Example C-1 | 8,700 | Example A-1 | 24 | 1.0 | 0.15 | 200,000 | 55 |
| Example C-2 | 8,700 | Example A-1 | 24 | 0.9 | 0.14 | 180,000 | 53 |
| Example C-3 | 8,700 | Example A-1 | 24 | 0.8 | 0.12 | 70,000 | 50 |
| Example C-4 | 8,700 | Example A-1 | 24 | 0.75 | 0.12 | 40,000 | 53 |
| Example C-5 | 8,700 | Example A-1 | 24 | 0.6 | 0.10 | 1,000 | 48 |

Examples C-6 to C-16

Water-soluble polyurethanes were synthesized in the same manner as in the example C-1, except that the type and amount of the comb-shaped hydrophobic diol put into the flask was different. However, for the PEG used in the examples C-11 and C-12, its molecular weight was a little different from the others' since its synthesis lot was different from the others'. In the examples C-13 and C-14, commercially available PEG#4000 (number average molecular weight 3,000) was used instead of PEG#6000. And in the examples C-15 and C-16, commercially available PEG#20000 (number average molecular weight 20,000) was used instead of PEG#6000.

The results are shown in Table C-2.

mPa·s) whose water-soluble polyurethane concentration is 2% by weight measured with a B type rotating viscometer at 6 rpm.

"Weight Average Molecular Weight" means the molecular weight measured by the GPC using monodisperse polystyrene as a standard reference material. As a solvent, chloroform was used.

When x is in the range of 0.01 to 0.5 and the weight average molecular weight is in the range of 100,000 to 1,000,000, water-soluble polyurethanes whose 2% aqueous solution viscosity is 1,000 to 500,000 mPa·s were obtained.

TABLE C-2

Example of Water-soluble Polyurethane Syntheses (2)

| Run Number | Molecular Weight of PEG | Type of Hydrophobic Diols | Total Number of Carbon Atoms of Hydrophobic Groups | Hydrophobic Diol/PEG (%) | Coefficient of Repeating Unit X | 2% Aqueous Solution Viscosity (mPa · s) | Weight Average Molecular Weight ($\times 10^4$) |
|---|---|---|---|---|---|---|---|
| Example C-6 | 8,700 | Example A-2 | 12 | 2.5 | 0.40 | 35,000 | 38 |
| Example C-7 | 8,700 | Example A-3 | 20 | 1.3 | 0.21 | 160,000 | 42 |
| Example C-8 | 8,700 | Example A-4 | 28 | 0.45 | 0.07 | 150,000 | 47 |
| Example C-9 | 8,700 | Example A-5 | 32 | 1.0 | 0.13 | 330,000 | 44 |
| Example C-10 | 8,700 | Example A-5 | 32 | 0.3 | 0.04 | 42,000 | 48 |
| Example C-11 | 8,500 | Example A-6 | 34 | 0.3 | 0.04 | 100,000 | 50 |
| Example C-12 | 8,500 | Example A-7 | 40 | 0.2 | 0.03 | 70,000 | 39 |
| Example C-13 | 3,000 | Example A-1 | 24 | 1.0 | 0.06 | 2,000 | 10 |
| Example C-14 | 3,000 | Example A-7 | 40 | 0.2 | 0.01 | 1,000 | 13 |
| Example C-15 | 20,000 | Example A-1 | 24 | 0.8 | 0.25 | 500,000 | 100 |
| Example C-16 | 20,000 | Example A-2 | 12 | 0.6 | 0.50 | 100,000 | 90 |

(Measurement of Setting Retardation Time)

Examples C-17 to C-19, Comparative Examples C-1, C-2

The setting retardation time of the water-soluble polyurethane obtained in the example C-1 and C-5 was measured and the measurements were compared with that of the commercially available cellulose ether.

The measurement was made on cement paste and mortar; however, since the results were almost the same in both cases, the results of the cement paste only will be shown below. The measurement was made in such a manner that a predetermined amount of thickening agent powder was added to and mixed with 100 g of normal portland cement, then 40 g of water was added and fully mixed, so as to obtain cement paste, the cement paste thus obtained was packed into a cylindrical insulating container, a thermocouple was inserted into the container around its center portion, and the variation of the internal temperature of the cement paste with time was recorded.

The results are shown in Table C-3.

TABLE C-3

Measurements of Setting Time

| Run Number | Type of Thickening Agent | Amount of Thickening Agent Added (% by weight of cement) | Peak Temperature of Heat Releasing (° C.) | Elapsed Time at Peak of Heat Releasing (hr) | Setting Retardation Time (hr) |
|---|---|---|---|---|---|
| Comparative example C-1 | None | — | 50 | 9.5 | 0 |
| Example C-17 | Example C-1 | 0.1 | 50 | 9.5 | 0 |
| Example C-18 | Example C-1 | 1 | 52 | 9.7 | 0.2 |
| Example C-19 | Example C-5 | 10 | 52 | 10.0 | 0.5 |
| Comparative example C-2 | Metholose 90SH-30000 | 1 | 44 | 16.5 | 7.0 |

Retardation of setting occurred in the cement paste using Metholose, which is a commercially available thickening agent, while it did not substantially occur in the cement paste using the thickening agents of the present invention. It is widely known that cellulose ethers cause setting retardation of cement, and the reason is generally considered to be the existence of a large number of hydroxyl groups on the polymer main chain. It is considered to be that, when there exist a large number of strong polar groups such as hydroxyl groups in a polymer, the polymer tends to bond strongly to calcium of the cement and the cement runs short of calcium content necessary for hydration reaction.

On the other hand the reasons that, in the cement paste using the underwater concrete thickening agent of the present invention, retardation of setting is not caused are not fully clarified; however, it is considered one of the reasons may be that ether groups as hydrophilic groups of the polymer main chain have relatively weak polarity and these groups do not bond to calcium strongly, accordingly, retardation of setting is not caused.

(Underwater Concrete Placing Test)

Examples C-20 to C-36, Comparative Examples C-3 to C-5

Tests were conducted using concrete comprising cement, sand, gravel, a thickening agent and water.

100 parts by weight of normal portland cement, 180 parts by weight of sand, 250 parts by weight of gravel and a predetermined amount of thickening agent were mixed with a concrete mixer. Then, 50 parts by weight of water was added to this composition, and further mixed, so as to obtain an underwater concrete composition. This concrete was allowed to freely fall underwater and packed into a cylindrical form 10 cm in diameter and 20 cm high sunk into a pool of 1 m deep. After 24 hours, this specimen was taken out of the water to remove the form and subjected to underwater curing, and its 7th day strength and 28th day strength were measured. And the presence of aggregate separation inside the specimen was observed.

Table C-4 shows the type of the thickening agents used in the examples and comparative examples, the amount of the same (% by weight to cement), the underwater anti-separation properties (capability of not allowing the aggregate to separate underwater) and the compressive strength after curing.

The presence of the aggregate separation was judged by observing the specimen before and after the measurement of the compressive strength. When observing no aggregate separation, the condition was judged to be good (A). When observing a little aggregate separation, but it was not so remarkable, the condition was judged to be fair (B). And when observing clear aggregate separation, the condition was judged to be failure (C).

For comparison, other examples are shown: two in which the commercially available typical cellulose ether thickening agent, methyl cellulose, 90SH-30000 manufactured by Shin-Etsu Chemical Co., Ltd. were used and the other one in which no thickening agent was used.

TABLE C-4

Results of Underwater Concrete Placing Tests (1)

| Run Number | Type of Thickening Agent | Amount of Thickening Agent added (% by weight of cement) | Underwater Anti-separation Properties | 7th Day Strength (kg/cm$^2$) | 28th Day Strength (kg/cm$^2$) |
|---|---|---|---|---|---|
| Example C-20 | Example C-1 | 0.5 | A | 246 | 342 |
| Example C-21 | Example C-3 | 1.0 | A | 248 | 355 |
| Example C-22 | Example C-5 | 5.0 | A | 255 | 365 |
| Example C-23 | Example C-1 | 0.1 | B | 245 | 340 |
| Example C-24 | Example C-3 | 0.2 | A | 250 | 372 |
| Example C-25 | Example C-5 | 10.0 | A | 238 | 362 |
| Example C-26 | Example C-6 | 1.0 | A | 238 | 345 |
| Example C-27 | Example C-7 | 0.5 | A | 241 | 343 |
| Example C-28 | Example C-8 | 1.0 | A | 232 | 338 |
| Example C-29 | Example C-9 | 0.1 | B | 236 | 358 |
| Example C-30 | Example C-10 | 1.0 | A | 242 | 348 |
| Example C-31 | Example C-11 | 1.0 | A | 238 | 354 |
| Example C-32 | Example C-12 | 1.0 | A | 245 | 338 |
| Example C-33 | Example C-13 | 5.0 | A | 245 | 348 |

TABLE C-4-continued

Results of Underwater Concrete Placing Tests (1)

| Run Number | Type of Thickening Agent | Amount of Thickening Agent added (% by weight of cement) | Underwater Anti-separation Properties | 7th Day Strength (kg/cm$^2$) | 28th Day Strength (kg/cm$^2$) |
|---|---|---|---|---|---|
| Example C-34 | Example C-14 | 10.0 | A | 237 | 346 |
| Example C-35 | Example C-15 | 0.2 | A | 243 | 356 |
| Example C-36 | Example C-16 | 0.2 | A | 239 | 361 |
| Comparative example C-3 | Metholose 90SH-30000 | 1.0 | A | 150 | 248 |

TABLE C-4-continued

Results of Underwater Concrete Placing Tests (1)

| Run Number | Type of Thickening Agent | Amount of Thickening Agent added (% by weight of cement) | Underwater Anti-separation Properties | 7th Day Strength (kg/cm$^2$) | 28th Day Strength (kg/cm$^2$) |
|---|---|---|---|---|---|
| Comparative example C-4 | Metholose 90SH-30000 | 0.1 | C | — | — |
| Comparative example C-5 | No Thickening Agent Added | — | C | — | — |

Comparing the examples and the comparative examples, it is obvious that the underwater concrete thickening agents according to the present invention have underwater anti-separation properties at least equivalent to and strength superior to the commercially available thickening agents (water-soluble cellulose ethers).

The underwater anti-separation properties may reflect the excellent thixotropic properties of the concrete. The reason is not fully clear; however, it is considered that the excellent thixotropic properties of the concrete (underwater concrete composition) according to the present invention reflect not only the high viscosity of the water-soluble polyurethane aqueous solution, but also the effects of the moderate interactions between the comb-shaped hydrophobic group of the water-soluble polyurethane and the cement particles.

For the strength after curing, the concrete of the present invention is particularly superior in initial strength to the concrete using the commercially available thickening agents. This may be because the concrete of the present invention does not cause retardation of setting.

Application to Ceramic Forming Binder
(Comb-shaped Hydrophobic Diols)

Besides comb-shaped hydrophobic diols A-1 to A-7 synthesized in the examples A-1 to A-7, comb-shaped hydrophobic diol D-1 synthesized in the following example D-1 was used.

Example D-1

Comb-shaped hydrophobic diol D-1 was synthesized in the same manner as in the example A-1, except that, instead of using 2-ethylhexylamine and 2-ethylhexylglycidyl ether, 2-ethylhexylglycidyl ether was added to dibutylaminopropylamine (Koei Chemical Co., Ltd.) in the ratio of 2:1 mole.

The results of the example D-1 are shown in Table D-1.

TABLE D-1

Examples of Arch-shaped Hydrophobic Diol Syntheses (1)
Structural Formula of Compounds:
R$^2$—OCH$_2$CH(OH)CH$_2$N(R$^1$)CH$_2$CH(OH)CH$_2$O—R$^3$

| Run Number | R$^1$ | R$^2$, R$^3$ | Molecular Weight obtained from OH value |
|---|---|---|---|
| Example D-1 | —(CH$_2$)$_3$N(CH$_2$)$_3$CH$_3$  └—(CH$_2$)$_3$CH$_3$ | —CH$_2$CH(CH$_2$)$_3$CH$_3$  └—CH$_2$CH$_3$ | 554 |

(Examples of Soluble Polyurethane Syntheses)

Examples of syntheses of soluble polyurethane using the hydrophobic diol of the example A-1 will be described below; however, it should be understood that these examples are not intended to limit the present invention.

Example D-2

100 g of commercially available PEG#6000 (available from JUNSEI CHEMICAL CO., LTD., number average molecular weight 8,700) was put into a 500 ml separable flask manufactured by SUS and was allowed to melt under nitrogen seal at 150° C. This molten PEG was subjected to drying under reduced pressure (3 mmHg) for 3 hours while stirring. The residual water content was 200 ppm. The temperature of the flask was reduced to 80° C., and 1.00 g of the comb-shaped hydrophobic diol A-1 obtained in the example A-1 and 2.28 g of hexamethylenediisocyanate (available from TOKYO KASEI KOGYO CO., LTD.) were put into the flask while stirring. When adding 0.01 g of DBTDL as a catalyst, the content of the flask was rapidly thickened after about 10 minutes. The reaction was allowed to progress for another two hours while stopping stirring.

After completion of the reaction, the product was taken out from the flask, cut into small pieces and allowed to stand to be cooled. The cooled product was further cooled with liquid nitrogen and pulverized into particles of diameter 1 mm (16 mesh) or smaller with an electric mill.

The weight average molecular weight of the product measured by the GPC was 500,000.

Examples D-3 to D-11

Soluble polyurethanes were synthesized in the same manner as in the example D-2, except that the comb-shaped hydrophobic diols A-2 to A-7 and D-1 were used. The amount of HDI was set so that the number of moles of HDI would become 1.00 times as large as the total number of moles of PEG and the comb-shaped hydrophobic diol (NCO/OH=1.00).

The results are shown in Table D-2.

TABLE D-2

Examples of Soluble Polyurethane Syntheses

| Run Number | Molecular Weight of PEG | Type of Hydrophobic Diol | Hydrophobic Diol/ PEG (%) | Coefficient of Repeating Unit X | Weight Average Molecular Weight ($\times 10^4$) |
|---|---|---|---|---|---|
| Example D-2 | 8,700 | Example A-1 | 0.80 | 0.12 | 50 |
| Example D-3 | 8,700 | Example A-2 | 2.00 | 0.34 | 34 |
| Example D-4 | 8,700 | Example A-3 | 1.00 | 0.16 | 38 |
| Example D-5 | 8,700 | Example A-4 | 0.50 | 0.07 | 43 |
| Example D-6 | 8,700 | Example A-5 | 0.30 | 0.04 | 51 |
| Example D-7 | 8,700 | Example A-6 | 0.80 | 0.10 | 35 |
| Example D-8 | 8,700 | Example A-7 | 0.60 | 0.07 | 45 |
| Example D-9 | 8,700 | Example D-1 | 2.00 | 0.24 | 30 |
| Example D-10 | 1,000 | Example A-7 | 0.72 | 0.01 | 1 |
| Example D-11 | 20,000 | Example A-2 | 1.66 | 0.50 | 100 |

In Table D-2, "Molecular Weight of PEG" means the number average molecular weight of PEG obtained from OH value (OHV).

"Hydrophobic Diol/PEG" means the weight ratio of the raw materials of the hydrophobic diol to PEG expressed as the percentage. "Coefficient of Repeating Unit x" means the coefficient x of the repeating unit having the aforementioned general formula 10.

"Weight Average Molecular Weight" means the molecular weight measured by the GPC using monodisperse polystyrene as a standard reference material. As a solvent, chloroform was used.

When x is in the range of 0.01 to 0.5 and the weight average molecular weight is in the range of 10,000 to 1,000,000, soluble polyurethanes are obtained.

(Extrusion of Ceramics)

Examples D-12 to D-21, Comparative Examples D-1 to D-3

In the examples, the composition of alumina green sand with the binder of the present invention was used as a ceramics forming binder. In the comparative examples, hydroxypropylmethyl cellulose (HPMC) was used as a binder.

The composition used in the tests was as follows:
Alumina: 100 parts by weight
Glycerol: 2 parts by weight
Binder: a predetermined amount of Table D-3
Water: 20 parts by weight
As a currently used binder, used was HPMC (Metholose 60SH-4000).

These compositions were extruded with a vacuum extruding machine (Miyazaki Iron Works, Ltd., FM-30) into plate-shaped forms 2 cm wide and 1 cm thick, and their formability was evaluated. The mark A indicates that extrusion is smoothly carried out and the surface topology of extruded forms is good, the mark B indicates that the surface topology of extruded forms is a little rough and the mark C indicates that the surface topology of extruded forms is rough or extrusion cannot be carried out.

The extruded forms were subjected to temporary calcination in the air at 500° C. The state where none of the 20 test pieces cracked in this calcination was expressed as A, the state where 1 to 2 test pieces cracked was expressed as B, and the state where 3 or more test pieces cracked was expressed as C.

The results are shown in Table D-3.

TABLE D-3

Composition of Green Sand and Test Results

| Run Number | Type of Binder | Amount of Binder Added (part by weight) | Formability | Yield after Temporary Calcination |
|---|---|---|---|---|
| Example D-12 | Example D-2 | 1.5 | A | A |
| Example D-13 | Example D-3 | 2.0 | A | A |
| Example D-14 | Example D-4 | 2.0 | A | A |
| Example D-15 | Example D-5 | 2.0 | A | A |
| Example D-16 | Example D-6 | 2.0 | A | A |
| Example D-17 | Example D-7 | 2.0 | A | A |
| Example D-18 | Example D-8 | 2.0 | A | A |
| Example D-19 | Example D-9 | 2.0 | A | A |
| Example D-20 | Example D-10 | 4.0 | A | A |
| Example D-21 | Example D-11 | 2.0 | A | A |
| Comparative Example D-1 | HPMC | 4.0 | A | C |
| Comparative Example D-2 | HPMC | 2.0 | B | B |
| Comparative Example D-3 | No Binder Added | — | C | *1 |

Notes
*1: The formability of the composition was bad and it could not be subjected to temporary calcination.

The compositions using the binders of the present invention have the formability equivalent to that of the compositions using the currently used binder. And the use of the binder of the present invention greatly improves the yield of the products in a calcination step.

(Thermal Analysis of Binder)

The improvement in the yield of products in a calcination step is related with the pyrolytic behavior of the binders. Accordingly, the pyrolytic behavior of the binders was evaluated by the TGA (thermogravimetric analysis) and the DTA (differential thermal analysis). FIG. D-1 shows the measurements by the TGA and FIG. D-2 shows the measurements by the DTA.

In FIG. D-1, the curve (a) represents the TGA measurements on the binder of the present invention and the curve (b) on the currently used binder, hydroxypropyl methyl cellulose. The measurement was carried out under air at a heating rate of 10° C./min. Table D-4 shows the carbon residue content at 500° C. and the thermal decomposition temperature at which the weight of the binders is decreased by 5% (Td5). Table D-4 also shows the measurements under nitrogen.

TABLE D-4

Pyrolytic Behavior of Binders

| Type of Binder | Under Air (10° C./min) | | Under Nitrogen (10° C./min) | |
|---|---|---|---|---|
| | Tg5 (° C.) | Carbon Residue Content (%) | Tg5 (° C.) | Carbon Residue Content (%) |
| Example D-2 | 228 | <1 | 372 | 1.5 |
| HPMC | 298 | <1 | 336 | 12 |

Tg5: Temperature at which the weight of the binders is decreased by 5%.
Carbon Residue Content: Amount of the carbonized polymer residue at 500° C..

Table D-4 shows that the binder of the present invention begins to be decomposed at low temperatures compared with the currently used binder and its carbon residue content is low, accordingly, degreasing can be carried out more effectively with the binder of the present invention.

In FIG. D-2, the curve (a) represents the DTA measurements on the binder of the present invention and the curve (b) on the currently used binder, hydroxypropyl methyl cellulose. The measurement was conducted under air at a heating rate of 10° C./min. The area of DTA curve is proportional to the heat value, and the calorific value of the binder of the present invention was 68% as high as that of the currently used binder (HPMC).

It is obvious that in the binder of the present invention, compared with the currently used binder, its heat release is moderate and its relative heat value is low, accordingly, the occurrence of thermal distortion in the extruded forms during the degreasing step (temporary calcination step) is a little.

It is clear from the above tests that the pyrolytic behavior of the binder of the present invention is moderate compared with the currently used binder, accordingly, the binder of the present invention contributes to the improvement in the yield of extruded forms during calcination, and hence, in productivity. Due to the moderate heat release and small heat value, the temperature of the extruded forms during calcination has a narrow distribution, which prevents thermal failure of the extruded forms. Further, since the heating rate can be increased, the productivity is improved.

The present invention is not intended to be limited to any specific ceramics, and ceramics applicable to the binders of the present invention include not only alumina, but also barium tianate, zirconia, silicon carbide, silicon nitride and other fine ceramics in general.

And there are many forming methods to which the binders of the present invention are applicable. Specifically, they are applicable not only to the extrusion process, but also to sheet forming, tape forming and pressing. Since they are thermoplastic resins, they can be used in injection molding. In any cases, they are superior to the currently used binders particularly in their moderate heat release during calcination.

The reasons have not been fully clarified yet that the heat release of the binders of the present invention during combustion is very moderate and the carbon residue content is low; however, presumably, the reasons are that urethane bond is susceptible to thermal decomposition, the elemental structures of the polymers contain a large number of oxygen, therefore, the heat generated due to oxidation is small, and that the molecules do not have a ring structure susceptible to carbonization.

Application to Moisturizer for Hair Cosmetics
(Comb-Shaped Hydrophobic Diols and Soluble Polyurethanes)

The above-described soluble polyurethanes D-2 to D-11 synthesized using the above-described comb-shaped hydrophobic diols A-1 to A-7 and D-1 were applied to hair conditioners, as described below.

(Hair Conditioners)

Examples E-1 to E-10, Comparative Examples E-1 to E-3

Examples of hair conditioners are shown below in which the soluble polyurethanes of the present invention are used as moisturizers for use in hair cosmetics. And as comparative examples, hair conditioners are shown in which polyethylene glycol (PEG) and hydroxyethyl cellulose (HEC) are used as moisturizers.

The compositions used in the tests are as follows.

Trimethylanmonium stearyl chloride: 1% by weight
Propylene Glycol: 5% by weight
Cetyl alcohol: 2% by weight
Oleyl alcohol EO adduct: 0.5% by weight
Moisturizer: predetermined amount shown in Table E-1
Perfume: proper amount
Preservatives: proper amount
Purified water: rest
Total: 100% by weight The feel of hair (moist hair impression) treated with the above composition was evaluated.

The mark A indicates that the moist hair impression was very satisfactory, the mark B was satisfactory and the mark C was bad.

The results are shown in Table E-1.

TABLE E-1

Formulation of Hair Conditioner and Test Results

| Run Number | Type of Moisturizer | Amount of Moisturizer Added (% by weight) | Moist Hair Impression after Drying | Remarks |
|---|---|---|---|---|
| Example E-1 | Example D-2 | 1.0 | A | |
| Example E-2 | Example D-3 | 0.5 | A | |
| Example E-3 | Example D-4 | 1.0 | A | |
| Example E-4 | Example D-5 | 1.0 | A | |
| Example E-5 | Example D-6 | 1.0 | A | |
| Example E-6 | Example D-7 | 0.5 | A | |
| Example E-7 | Example D-8 | 1.0 | A | |
| Example E-8 | Example D-9 | 0.5 | A | |
| Example E-9 | Example D-10 | 1.5 | A | |
| Example E-10 | Example D-11 | 0.5 | B | |
| Example E-1 | PEG | 1.5 | C | Oily feel |
| Example E-2 | HEC | 1.0 | C | Dry feel |
| Example E-3 | No moisturizer added | — | C | |

The use of the currently used moisturizer cannot impart moist feel to hair, but oily feel or dry feel. On the other hand, the use of the moisturizer of the present invention can impart soft feel to hair, neither oily feel nor dry feel.

What is claimed is:

1. Water-soluble polyurethane comprising a repeating unit (U-1) represented by the following general formula (1):

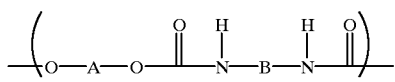

and a repeating unit (U-2) represented by the following general formula (2)

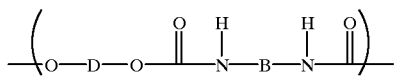

wherein the molar ratio of (U-1) to (U-2) is 0.5–0.999 to 0.001–0.5, wherein the sum of the respective values of (U-1) and (U-2) is one, and the weight average molecular weight, as determined by GPC, is in the range of 10,000 to 10,000,000, wherein A is a bivalent group such that HO-A-OH is a water-soluble polyoxyalkylene polyol having hydroxyl groups on both ends and having a number average molecular weight of 400 to 100,000 (compound A), and said bivalent group A is optionally further substituted with at least one hydroxyl group, B is a bivalent group such that OCN-B-NCO is a polyisocyanate compound selected from the group consisting of polyisocyanates whose total number of carbon atoms is 3 to 18 (compound B), and D is a bivalent group such that HO-D-OH is comb-shaped hydrophobic diol having the following general formula (3) (compound D):

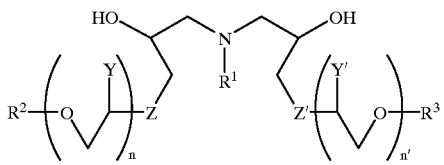

wherein $R^1$ is a hydrocarbon group or a nitrogen-containing hydrocarbon group of 1 to 20 carbon atoms; each of $R^2$ and $R^3$ is a hydrocarbon group of 4 to 21 carbon atoms; part of or all of the hydrogen atoms of the hydrocarbon groups $R^1$, $R^2$ and $R^3$ are optionally substituted by fluorine, chlorine, bromine, or iodine; $R^2$ and $R^3$ are the same or different from each other; each of Y and Y' is hydrogen, a methyl group or a $CH_2Cl$ group; Y and Y' are the same or different from each other; each of Z and Z' is oxygen, sulfur or a $CH_2$ group; Z and Z' are the same or different from each other; n is an integer of 0 to 15 when Z is oxygen and is 0 when Z is sulfur or a $CH_2$ group; n' is an integer of 0 to 15 when Z' is oxygen and is 0 when Z' is sulfur or a $CH_2$ group; and n and n' are the same or different from each other.

2. The water-soluble polyurethane as claimed in claim 1, wherein the molar ratio of (U-1) to (U-2) is 0.5–0.99 to 0.01–0.5, wherein the sum of the respective values of (U-1) and (U-2) is one, said compound A is polyethylene glycol whose number average molecular weight is 3,000 to 20,000, said compound B is a diisocyanate compound selected from the group consisting of aliphatic diisocyanates whose total number of carbon atoms is 3 to 18, and the water-soluble polyurethane has a weight average molecular weight, as determined by GPC, in the range of 100,000 to 1,000,000.

3. The water-soluble polyurethane as claimed in claim 1 or 2, wherein said compound D is comb-shaped hydrophobic diol having the following formula (4):

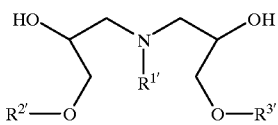

wherein $R^{1'}$ is a chain alkyl group of 4 to 18 carbon atoms, each of $R^{2'}$ and $R^{3'}$ is an alkyl group or aryl group of 4 to 18 carbon atoms, the total number of carbon atoms of $R^{1'}$, $R^{2'}$ and $R^{3'}$ is 12 to 40, and $R^2$ and $R^3$ are the same.

4. The water-soluble polyurethane as claimed in claim 1 or 2, wherein said compound D is comb-shaped hydrophobic diol having the following formula (5)

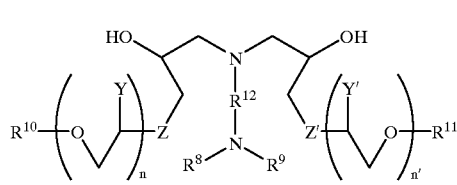

wherein $R^8$ and $R^9$ are hydrocarbon groups, the total number of the carbon atoms of $R^8$ and $R^9$ being 2 to 20; $R^{10}$ and $R^{11}$ are hydrocarbon groups each of 4 to 21 carbon atoms; part of or all of the hydrogen atoms of the hydrocarbon groups $R^8$, $R^9$, $R^{10}$ and $R^{11}$ are optionally substituted by fluorine, chlorine, bromine or iodine; $R^8$ and $R^9$ are the same or different from each other; $R^{10}$ and $R^{11}$ are the same or different from each other; $R^{12}$ is an alkylene group of 2 to 7 carbon atoms; each of Y and Y' is hydrogen, a methyl group or a $CH_2Cl$ group; Y and Y' may be the same or different from each other; each of Z and Z' is oxygen, sulfur or a $CH_2$ group; Z and Z' are the same or different from each other; n is an integer of 0 to 15 when Z is oxygen and is 0 when Z is sulfur or a CH, group; n' is an integer of 0 to 15 when Z' is oxygen and is 0 when Z' is sulfur or a $CH_2$ group; and n and n' are the same or different from each other.

5. The water-soluble polyurethane as claimed in claim 1 or 2, wherein said compound B is hexamethylenediisocyanate, isophoronediisocyanate, hydrogenated tolylenediisocyanate, hydrogenated xylylenediisocyanate, or norbornanediisocyanato methyl.

6. An extruding auxiliary for a cement material comprising the water-soluble polyurethane as claimed in claim 1.

7. The extruding auxiliary for a cement material as claimed in claim 6, wherein said water-soluble polyurethane has a viscosity of 2.5% aqueous solution at 25° C. of 1,000 to 1,000,000 mPa·s.

8. A mortar thickening agent, comprising the water-soluble polyurethane as claimed in claim 1.

9. The mortar thickening agent as claimed in claim 8, wherein in said water-soluble polyurethane, the molar ratio of (U-1) to (U-2) is 0.5–0.99 to 0.01–0.5, wherein the sum of the respective values of (U-1) and (U-2) is one, and a viscosity of 2% aqueous solution at 20° C. is in the range of 10 mPa·s to 300,000 mPa·s.

10. The mortar thickening agent as claimed in claim 8 or 9, wherein said water soluble polyalkylene polyol is polyethylene glycol having a number average molecular weight of 1,000 to 20,000.

11. The mortar thickening agent as claimed in claim 8 or 9, wherein said polyisocyanate compound is a chain aliphatic diisocyanate or an alicyclic diisocyanate.

12. The mortar thickening agent as claimed in claim 8 or 9, wherein said polyisocyanate compound is a compound selected from the group consisting of hexamethylenediisocyanate, isophoronediisocyanate, hydrogenated tolylenediisocyanate, hydrogenated xylylenediisocyanate, and norbornanediisocyanato methyl.

13. The mortar thickening agent as claimed in claim 8 or 9, wherein said compound D is a comb-shaped hydrophobic diol represented by the following general formula (6)

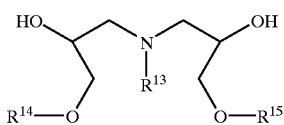

(6)

wherein $R^{13}$ is a straight-chain or branched-chain alkyl group of 4 to 18 carbon atoms, each of $R^{14}$ and $R^{15}$ is a straight-chain or branched chain alkyl group of 4 to 18 carbon atoms, and the alkyl groups $R^{14}$ and $R^{15}$ are the same or different from each other.

14. An underwater concrete thickening agent comprising the water-soluble polyurethane as claimed in claim 1.

15. The underwater concrete thickening agent as claimed in claim 14, wherein in said water-soluble polyurethane, the molar ratio of (U-1) to (U-2) is 0.5–0.99 to 0.01–0.5, wherein the sum of the respective values of (U-1) and (U-2) is one, and the weight average molecular weight of the polyurethane, as determined by GPC, is in the range of 100,000 to 1,000,000.

16. The underwater concrete thickening agent as claimed in claim 14 or 15, wherein said compound D is a comb-shaped hydrophobic diol represented by the following formula (4)

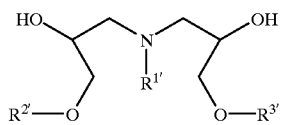

(4)

wherein $R^{1'}$ is a chain alkyl group of 4 to 18 carbon atoms, each of $R^{2'}$ and $R^{3'}$ is an alkyl group or aryl group of 4 to 18 carbon atoms, the total number of carbon atoms of $R^{1'}$, $R^{2'}$ and $R^{3'}$ is 12 to 40, and $R^{2'}$ and $R^{3'}$ are the same.

17. The underwater concrete thickening agent as claimed in claim 14 or 15, wherein said polyisocyanate compound is a chain aliphatic diisocyanate or an alicyclic diisocyanate.

18. The underwater concrete thickening agent as claimed in claim 14 or 15, wherein said polyisocyanate compound is a compound selected from the group consisting of hexamethylenediisocyanate, isophoronediisocyanate, hydrogenated tolylenediisocyanate, hydrogenated xylylenediisocyanate, and norbornanediisocyanato methyl.

19. The underwater concrete thickening agent as claimed in claim 14 or 15, wherein said water-soluble polyurethane has a viscosity of 2% aqueous solution at 20° C. in the range of 1,000 to 500,000 mPa·s.

20. A ceramics forming binder comprising a water-soluble polyurethane as claimed in claim 1.

21. The ceramics forming binder as claimed in claim 20, wherein in said water-soluble polyurethane, the molar ratio of (U-1) to (U-2) is 0.5–0.99 to 0.01–0.5, wherein the sum of the respective values of (U-1) and (U-2) is one, and the weight average molecular weight of the polyurethane, as determined by GPC, is in the range of 10,000 to 1,000,000.

22. The ceramics forming binder as claimed in claim 20 or 21, wherein said water-soluble polyalkylene polyol is polyethylene glycol of a number average molecular weight of 1,000 to 20,000 and said polyisocyanate compound is a chain aliphatic diisocyanate or an alicyclic diisocyanate.

23. The ceramics forming binder as claimed in claim 20 or 21, wherein said polyisocyanate compound is a compound selected from the group consisting of hexamethylenediisocyanate, isophoronediisocyanate, hydrogenated tolylenediisocyanate, hydrogenated xylylenediisocyanate and norbornanediisocyanato methyl.

24. The ceramics forming binder as claimed in claim 20 or 21 for use as a binder for ceramics extrusion.

25. A moisturizer for hair cosmetics comprising the water-soluble polyurethane as claimed in claim 1.

26. The moisturizer for hair cosmetics as claimed in claim 25, wherein in said water-soluble polyurethane, the molar ratio of (U-1) to (U-2) is 0.5–0.99 to 0.01–0.5, wherein the sum of the respective values of (U-1) and (U-2) is one, and weight average molecular weight of the polyurethane, as determined by GPC, is in the range of 10,000 to 1,000,000.

27. The moisturizer for hair cosmetics as claimed in claim 25 or 26, wherein said water-soluble polyoxyalkylene polyol is polyethylene glycol having a number average molecular weight of 400 to 20,000 and said polyisocyanate compound is a chain aliphatic diisocyanate or an alicyclic diisocyanate.

28. The moisturizer for hair cosmetics claimed in claim 25 or 26, wherein said polyisocyanate compound is a compound selected from the group consisting of hexamethylenediisocyanate, isophoronediisocyanate, hydrogenated tolylenediisocyanate, hydrogenated xylylenediisocyanate and norbornanediisocyanato methyl.

* * * * *